United States Patent
Pujara

(10) Patent No.: US 9,801,891 B2
(45) Date of Patent: *Oct. 31, 2017

(54) COMPOSITIONS AND METHODS FOR LOWERING INTRAOCULAR PRESSURE

(71) Applicant: ALLERGAN, INC., Irvine, CA (US)

(72) Inventor: Chetan P. Pujara, Irvine, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/347,532

(22) Filed: Nov. 9, 2016

(65) Prior Publication Data

US 2017/0065610 A1 Mar. 9, 2017

Related U.S. Application Data

(63) Continuation of application No. 14/147,302, filed on Jan. 3, 2014, now Pat. No. 9,522,153, which is a continuation-in-part of application No. 13/698,182, filed as application No. PCT/US2010/061563 on Dec. 21, 2010, now abandoned.

(60) Provisional application No. 61/361,749, filed on Jul. 6, 2010, provisional application No. 61/288,936, filed on Dec. 22, 2009.

(51) Int. Cl.
| | |
|---|---|
| A61K 31/498 | (2006.01) |
| A61K 31/5377 | (2006.01) |
| A61K 31/5575 | (2006.01) |
| A61K 9/00 | (2006.01) |
| A61K 47/02 | (2006.01) |
| A61K 47/12 | (2006.01) |
| A61K 47/18 | (2017.01) |
| A61K 9/08 | (2006.01) |

(52) U.S. Cl.
CPC ........ *A61K 31/5575* (2013.01); *A61K 9/0048* (2013.01); *A61K 9/08* (2013.01); *A61K 31/498* (2013.01); *A61K 31/5377* (2013.01); *A61K 47/02* (2013.01); *A61K 47/12* (2013.01); *A61K 47/186* (2013.01)

(58) Field of Classification Search
CPC .............. A61K 31/498; A61K 31/5377; A61K 31/5575
See application file for complete search history.

(56) References Cited

U.S. PATENT DOCUMENTS

| | | | |
|---|---|---|---|
| 3,890,319 A | 6/1975 | Danielewicz et al. |
| 4,029,792 A | 6/1977 | Danielewicz et al. |
| 4,055,602 A | 10/1977 | Nelson |
| 4,100,192 A | 7/1978 | Morozowich |
| 4,122,282 A | 10/1978 | Nelson |
| 4,123,441 A | 10/1978 | Johnson |
| 4,128,577 A | 12/1978 | Nelson |
| 4,171,331 A | 10/1979 | Biddlecom et al. |
| 4,183,870 A | 1/1980 | Caton et al. |
| 4,195,085 A | 3/1980 | Stone |
| 4,256,745 A | 3/1981 | Skuballa et al. |
| 4,303,796 A | 12/1981 | Nelson |
| 4,382,953 A | 5/1983 | Ishii et al. |
| 4,543,353 A | 9/1985 | Faustini et al. |
| 4,599,353 A | 7/1986 | Bito |
| 4,812,457 A | 3/1989 | Narumiya et al. |
| 4,861,760 A | 8/1989 | Mazuel et al. |
| 4,910,225 A | 3/1990 | Ogawa et al. |
| 4,994,274 A | 2/1991 | Chan et al. |
| 5,021,410 A | 6/1991 | Burke |
| 5,028,624 A | 7/1991 | Chan et al. |
| 5,034,413 A | 7/1991 | Chan et al. |
| 5,215,991 A | 6/1993 | Burke |
| 5,281,591 A | 1/1994 | Burke |
| 5,290,781 A | 3/1994 | Espino et al. |
| 5,352,708 A | 10/1994 | Woodward et al. |
| 5,459,140 A | 10/1995 | Gramer |
| 5,474,979 A | 12/1995 | Ding et al. |
| 5,502,052 A | 3/1996 | DeSantis |
| 5,510,383 A | 4/1996 | Bishop et al. |
| 5,545,665 A | 8/1996 | Burk |
| 5,564,596 A | 10/1996 | Meadows et al. |
| 5,587,391 A | 12/1996 | Burk |
| 5,607,978 A | 3/1997 | Woodward et al. |
| 5,688,819 A | 11/1997 | Woodward et al. |
| 5,795,913 A | 8/1998 | Lehmussaari et al. |
| 5,827,862 A | 10/1998 | Yamamura et al. |
| 5,856,329 A | 1/1999 | Wheeler et al. |
| 5,883,108 A | 3/1999 | DeSantis |
| 6,146,622 A | 11/2000 | Castillo et al. |
| 6,159,458 A | 12/2000 | Bowman et al. |
| 6,174,524 B1 | 1/2001 | Bawa et al. |

(Continued)

FOREIGN PATENT DOCUMENTS

| | | |
|---|---|---|
| CA | 2144967 | 3/1994 |
| CA | 2225626 | 1/1997 |

(Continued)

OTHER PUBLICATIONS

"United States District Court for the Eastern District of Texas Marshall Division, Finding of Facts and Conclusions of Law" *Allergan v. Sandoz*; Aug. 22, 2011.
Adkins, Julie, Brimonidine—a review of its pharmacological properties and clinical potential in the management of open-angle glaucoma and ocular hypertension, Drugs Aging, 1998, 225-241, 12.
Airaksinen, Juhani et al, A Double Masked Study of Timolol and Pilocarpine Combined, American Journal of Ophthalmology, Dec. 15, 1987, 587-590, 104.

(Continued)

*Primary Examiner* — Zohreh Fay
(74) *Attorney, Agent, or Firm* — Lorenz Siddiqi

(57) ABSTRACT

Disclosed herein are compositions for lowering intraocular pressure (IOP) of an eye comprising a combination IOP-lowering agents bimatoprost, brimonidine, and timolol. Further disclosed are methods for reducing IOP in the eye of a subject.

6 Claims, No Drawings

(56) References Cited

U.S. PATENT DOCUMENTS

| | | |
|---|---|---|
| 6,194,415 B1 | 2/2001 | Wheeler et al. |
| 6,242,442 B1 | 6/2001 | Dean et al. |
| 6,248,741 B1 | 6/2001 | Wheeler et al. |
| 6,277,829 B1 | 8/2001 | Asero et al. |
| 6,294,563 B1 | 9/2001 | Garst |
| 6,316,441 B1 | 11/2001 | Dean et al. |
| 6,403,649 B1 | 6/2002 | Woodward et al. |
| 6,410,045 B1 | 6/2002 | Schultz et al. |
| 6,440,964 B1 | 8/2002 | Cagle et al. |
| 6,441,047 B2 | 8/2002 | DeSantis |
| 6,562,873 B2 | 5/2003 | Olejnik et al. |
| 6,596,765 B2 | 7/2003 | Ueno |
| 6,627,210 B2 | 9/2003 | Olejnik et al. |
| 6,646,001 B2 | 11/2003 | Hellberg et al. |
| 6,740,664 B2 | 5/2004 | Cagle et al. |
| 6,743,439 B1 | 6/2004 | Castillo et al. |
| 6,933,289 B2 | 8/2005 | Lyons et al. |
| 7,030,149 B2 | 4/2006 | Chang et al. |
| 7,320,976 B2 | 1/2008 | Chang et al. |
| 7,323,463 B2 | 1/2008 | Chang et al. |
| 7,642,258 B2 | 1/2010 | Chang et al. |
| 7,851,504 B2 | 12/2010 | Chang et al. |
| 8,017,655 B2 | 9/2011 | Woodward et al. |
| 8,278,353 B2 | 10/2012 | Chang et al. |
| 8,299,118 B2 | 10/2012 | Chang et al. |
| 8,309,605 B2 | 11/2012 | Chang et al. |
| 2002/0013294 A1 | 1/2002 | DeLong et al. |
| 2002/0071874 A1 | 6/2002 | Olejnik et al. |
| 2002/0103255 A1 | 8/2002 | Hellberg et al. |
| 2002/0128267 A1 | 9/2002 | Bandyopadhyay et al. |
| 2002/0177625 A1 | 11/2002 | O'Donnell et al. |
| 2004/0029771 A1 | 2/2004 | Rigdon et al. |
| 2004/0079671 A1 | 4/2004 | Bandyopadhyay et al. |
| 2004/0115234 A1 | 6/2004 | Gewirtz |
| 2005/0004074 A1 | 1/2005 | Lyons et al. |
| 2005/0276867 A1 | 12/2005 | Lyons et al. |
| 2006/0141049 A1 | 6/2006 | Lyons et al. |
| 2006/0211770 A1 | 9/2006 | Chang et al. |
| 2009/0149546 A1 | 6/2009 | Chang et al. |
| 2011/0124737 A1 | 5/2011 | Chang et al. |
| 2012/0316243 A1 | 12/2012 | Chang et al. |

FOREIGN PATENT DOCUMENTS

| | | |
|---|---|---|
| CA | 2440764 | 10/2003 |
| CA | 2498233 | 3/2004 |
| DE | 2721534 | 12/1977 |
| DE | 4201079 | 7/1993 |
| EP | 0093380 | 11/1983 |
| EP | 0102230 | 3/1984 |
| EP | 0098141 | 11/1984 |
| EP | 0253094 | 1/1988 |
| EP | 0364417 | 4/1990 |
| EP | 0426390 | 8/1991 |
| EP | 0453127 | 10/1991 |
| EP | 1496912 | 10/2003 |
| EP | 2033649 | 11/2009 |
| FR | 2239458 | 2/1975 |
| FR | 2312240 | 12/1976 |
| FR | 2386523 | 11/1978 |
| FR | 2402644 | 4/1979 |
| GB | 1402035 | 8/1975 |
| JP | S49-069636 | 7/1974 |
| JP | S62-215537 | 9/1987 |
| JP | 2004-002358 | 1/2004 |
| LU | 68940 | 12/1973 |
| WO | 90-02553 | 3/1990 |
| WO | 92-08465 | 5/1992 |
| WO | 94-06433 | 3/1994 |
| WO | 95-16449 | 6/1995 |
| WO | 02-07731 | 1/2002 |
| WO | 03-074038 | 9/2003 |
| WO | 03-088973 | 10/2003 |
| WO | 03088973 A1 | 10/2003 |
| WO | 2004-013119 | 2/2004 |
| WO | 2008006235 | 1/2008 |

OTHER PUBLICATIONS

Alcon Laboratories, Inc., Travatan® (Travoprost Ophthalmic Solution) 0.004% Sterile, Package Labeling, 2004, 7 Pages, NDA 21-257.

*Allergan, Inc. v. Sandoz In., Alcon Laboratories, Inc., Alcon Research, Ltd., Alcon, Inc., and Falcon Pharmaceuticals, Ltd., and Apotex Inc. And Apotex Corp., and Watson Laboratories, Inc.*, (Fed. Cir. 2013) 20 Pages.

Allergan, Inc., Lumigan (Allergan) (Bimatoprost Ophthalmic Solution) 0.03% Product Monograph, Physicians' Desk Reference, 2001, 7 Pages.

Allergan, Inc., Lumigan Package Insert, NDA 21-275, Mar. 2001, 6 Pages, NDA 21-275.

Alm, Albert et al, Uveoscleral Outflow—A Review, Experimental Eye Research, 2009, 760-768, 88(4).

Alphagan (Brimonidine Tartrate Ophthalmic Solution) 0.5%, Information Leaflet by Allergan, 2001, 17 Pages.

Arici, MK et al, A Short Term Study of the Additive Effect of Timolol and Brimonidine on Intraocular Pressure, Eye 2002, Jan. 1, 2002, 39-43, 16 (1), Nature Publishing Group.

Arndt, H.C., The Synthesis and Biological Activity of Prostaglandin Analogs Containing Spirocyclic Rings, Prostaglandins, 1977, 837-843, 13 (5).

Arvo, 1999 Annual Meeting Fort Lauderdale, Florida May 9-May 14, Association for Research in Vision and Ophthalmology, Mar. 15, 1999, 4, 40(4), US.

Arvo, 2001 Annual Meeting Fort Lauderdale, Florida Apr. 29-May 4, Investigative Ophthalmology & Visual Science, Mar. 15, 2001, S822, 2 pgs, 42(4), The Association for Research in Vision and Ophthalmology, US.

Ashton, Paul et al, Formulation Influence on Conjunctival Penetration of Four Beta Blockers in the Pigmented Rabbit: A Comparison with Corneal Penetration, Pharmaceutical Research, 1991, 1166-1174, 8 (9).

Barnebey, Howard et al, The Efficacy of Brimonidine in Decreasing Elevations in Intraocular Pressure after Laser Trabeculoplasty, Ophthalmology, 1993, 1083-1088, 100 (7).

Baudouin, Christophe, Side Effects of Antiglaucomatous Drugs on the Ocular Surface, Cur Op Ophth, 1996, 80-86, 7 (2).

Bean, Gerald, Commercially Available Prostaglandin Analogs For The Reduction of Intraocular Pressure: Similarities and Differences, Survey of Ophthalmology, 2008, S69-S84, 53 (Supp. 1).

Berglund, Barbara et al, Investigation of Structural Analogs of Prostaglandin Amides for Binding to and Activation of CB1 and CB2 Cannabinoid Receptors in Rat Brain and Human Tonsils, Adv Exp Med Biol, 1999, 527-533, 469.

Betoptic® Pilo Ophthalmic Suspension Product Information, Alcon Labs., Inc., 1997.

Bhatt, R. et al, Prospective Survey of Adverse Reactions to Topical Antiglaucoma Medications in a Hospital Population, Eye, 2005, 392-395, 19.

Bito, L.Z. et al, The Ocular Pharmacokinetics of Eicosanoids and Their Derivatives. 1. Comparison of Ocular Eicosanoid Penetration and Distribution Following the Topical Application of PGF2α, PGF2α-1-methyl Ester, and PGF2α-1-Isopropyl Ester, Exp. Eye Res., 1987, 217-226, 44.

Bito, L.Z. et al, Prostaglandins, Other Eicosanoids, and Their Derivatives as Potential Antiglaucoma Agents, Glaucoma: Applied Pharmacology in Medical Treatment, 1984, 477-505, n/a.

Bito, L.Z., Biological Protection with Prostanoids, CRC Press, Inc., 1985, 231-252, 1, Cohen, M. M., ed., Boca Raton, FL.

Bito, L.Z., Prostaglandins, Old Concepts And New Perspectives, Archives Of Ophthalmology, 1987, 1036-1039, 105.

BNF, Local Anaesthetics, British National Formulary, Mar. 2002, p. 514, 3 scanned pgs, 43, British Medical Association.

Boyd, James, Quantitative Comparison of Methods of Administering Physostigmine, Archives Ophthalmology, 1943, 521-525, 30(4).

(56) References Cited

OTHER PUBLICATIONS

Brandt, James et al, Comparison of Once- or Twice-Daily Bimatoprost with Twice-Daily Timolol in Patients with Elevated IOP, American Academy of Ophthalmology, 2001, 1023-1031, 108(6).
Bressler, Neil et al, Age-Related Macular Degeneration, Surv. Ophthalmol., 1988, 375-413, 32 (6).
Bressler, Susan et al, Age-related Macular Degeneration: Drusen and Geographic Atrophy, Principles and Practice of Ophthalmology, 1994, 826-833, 2.
Brown, Michael, Control of Contamination in Ophthalmic Solutions, Proc. R. Sco. Med., 1967, 354-357, 60.
Brubaker, Richard et al, Effects of AGN 192024, a new Ocular Hypotensive Agent, on Aqueous Dynamics, American journal of Ophthalmology, 2001, 19-24, 131(1).
Burger, Artur et al, Hunnius Pharmazeutisches Worterbuch, 1998, 1000-1001, 102-103.
Burke, J.A. et al, Ocular Effects of a Relatively Selective α-2 Agonist (UK-14, 304-18) in Cats, Rabbits, and Monkeys, Current Eye Research, 1986, 665-676, 5(9).
Burke, J.A. et al, Preclinical Evaluation of Brimonidine, Survey of Ophthalmology, Nov. 1996, S9-S18, 41(1).
Burstein, Neal, Electrophysiologic and Morphologic Effects of Ophthalmic Preparations on Rabbit Cornea Epithelium, Invest Ophthalmol Visual Sci, 1977, 899-911, 16 (10).
Burstein, Neal, Preservative Alteration of Corneal Permeability in Humans and Rabbits, Investigative Ophthalmology & Visual Science, Dec. 1984, 1453-1457, 25(12).
Burstein, Neal, Preservative Cytotoxic Threshold For Benzalkonium Chloride and Chlorhexidine Digluconate in Cat and Rabbit Corneas, Invest. Ophthal. & Visual Sci., 1980, 308-313, 19 (3).
Cadet, Patrick et al, Molecular Identification and Functional Expression of μ3, a Novel Alternatively Spliced Variant of the Human μ Opiate Receptor Gene, J. Immunol., 2003, 5118-5123, 170.
Camber, Ola et al, Influence of Some Preservatives on the Corneal Permeability of Pilocarpine and Dexamethasone, in Vitro, International Journal of Pharmaceutics, 1987, 229-234, 39.
Camras, Carl B., Reduction of Intraocular Pressure By Prostaglandins Applied topically To The Eyes Of Conscious Rabbits, Investigative Ophthalmology & Visual Science, Dec. 1977, 1125-1134, 16(12), US.
Camras, Carl B. et al, Bimatoprost, the Prodrug of a Prostaglandin Analogue, Br J Ophthalmol, 2008, 862-863, 92.
Camras, Carl B. et al, Detection of the Free Acid of Bimatoprost in Aqueous Humor Samples From Human Eyes Treated with Bimatoprost Before Cataract Surgery, The American Academy of Ophthalmology, 2004, 2193-2198, 7pg.
Camras, Carl B. et al, Reduction of Intraocular Pressure in Normal and Glaucomatous Primate (*Aotus trivirgatus*) Eyes By Topically Applied Prostaglandin F2α, Current Eye Research, 1981, 205-209, 1 (4).
Camras, Carl B. et al, Intraocular Pressure Reduction with PhXA34, a New Prostaglandin Analogue, in Patients With Ocular Hypertension, Arch Ophthalmol, 1992, 1733-1738, 110.
Cantor, Louis et al, Comparison of the Effect of Alphagan 0.2% versus Trusopt 2.0% in Combination with Beta-Blockers, Investigative Ophthalmology & Visual Science, Mar. 1998, S480, 39(4).
Cantor, Louis et al, Bimatoprost: A Member of a New Class of Agents, The Prostamides, For Glaucoma Management, Exp. Opin. Invest. Drugs, 2001, 721-731, 10 (4).
Cantor, Louis et al, Brimonidine, Exp. Opin. Invest. Drugs., 1997, 1063-1083, 6(8).
Cantor, Louis et al, Levels of Bimatoprost Acid in the Aqueous Humour After Bimatoprost Treatment of Patients with Cataract, Br. J. Ophthalmol, 2007, 629-632, 91.
Cantor, Louis et al, Reply-Bimatoprost, the Prodrug of a Prostaglandin Analogue, Br J Ophthalmol, 2008, 863-864, 92.
Cantor, Louis, The Evolving Pharmacotherapeutic Profile of Brimonidine, an α2-adrenergic Agonist, After Four Years of Continuous Use, Expert Opinion on Pharmacotherapy, 2000, 815-834, 1(4).
Center for Drug Evaluation and Research, Application No. 21-398, Summary Review, 2007.
Center for Drug Evaluation and Research, Application No. 21,398, Statistical Reviews, 2007.
Center for Drug Evaluation and Research, Application No. 21-398, Approvable Letter, 2006.
Center for Drug Evaluation and Research, Application No. 21-398, Medical Reviews, 2007.
Center for Drug Evaluation and Research, Summary Review of Application No. 22-184 (Lumigan 0.01%) (Jul. 2010).
Centofanti, M. et al, Comparative Acute Effects of 0.2% Brimonidine versus 2% Dorzolamide Combined to Beta-Blockers in Ocular Hypertension, Investigative Ophthalmology & Visual Science, Mar. 1998, S480, 39(4).
Chang-Lin, Joan-En et al, Aqueous Humor Penetration of Topical Bimatoprost 0.01% and Bimatoprost 0.03% in Rabbits: Response to Authors, Clinical Ophthalmology, Aug. 9, 2011, 1119-1120, 5.
Cheng-Bennett, A. et al, Studies on a Novel Series of Acyl Ester Prodrugs of Prostaglandin F2α, British Journal of Ophthalmology, 1994, 560-567, 78.
Choudhri, Saira et al, A Comparison of Dorzolamide-Timolol Combination Versus the Concomitant Drugs, American Journal of Ophthalmology, Dec. 2000, 833, 130(6).
Cioffi, George et al, Microvasculature of the Anterior Optic Nerve, Surv. Ophthalmol., May 1994, S107-S117, 38.
Clineschmidt, Coleen et al, A Randomized Trial in Patients Inadequately Controlled with Timolol Alone Comparing the Dorzolamide-Timolol Combination to Monotherapy with Timolol or Dorzolamide, American Journal of Ophthalmology, Oct. 1998, 1952-1959, 96(11).
Clinical Study Report: A Multicenter, Double-Masked, Randomized, Parallel Study of the Safety and Efficacy of 0.2% Brimonidine Tartrate/0.5% Timolol Combination Ophthalmic . . . , 2008, 11 Pages.
Coakes, Roger et al, The Mechanism of Timolol in Lowering Intraocular Pressure in the Normal Eye, Arch. Opthalmol., Nov. 1978, 2045-2048, 96(11).
Collin, Barry, Ultrastructural Changes to Corneal Stromal Cells Due to Ophthalmic Preservatives, ACTA Ophthalmologic, 1986, 72-78, 64.
Combigan Product Label, Allergan, Inc., 11 pages, 2008.
Connor, Jennie et al, Driver Sleepiness and Risk of Serious Injury to Car Occupants: Population Based Case Control Study, BMJ, May 11, 2002, 5 Pages, 324.
Costagliola, Ciro et al, Ocular Surface Changes Induced By Topical Application of Latanoprost and Timolol: A Short-Term Study in Glaucomatous Patients With And Without Allergic Conjunctivitis, Graefe's Arch Clin Exp Ophthalmol, 2001, 809-814, 239.
Craven, Randy, Efficacy and Safety of the IOP-Lowering Fixed Combination Brimonidine 0.2%/Timolol 0.5%, M200510403E.1. doc, 2005, One page.
Craven, Randy et al, Brimonidine and Timolol Fixed-Combination Therapy Versus Monotherapy: A-Month Randomized Trial in Patients with Glaucoma or Ocular Hypertension, Journal of Ocular Pharmacology and Therapeutics, 2005, 337-348, 21(4).
Crowston, Jonathan et al, Effect of Bimatoprost on Intraocular Pressure in prostaglandin FP Receptor Knockout Mice, Investigative Ophthalmology & Visual Science, 2005, 4571-4577, 46.
Cruz, Dra. IBIS Sedeno et al, Estudio De La Eficacia Clinica De La Brimonidina Vs Timolol En El Tratamiento Del Glaucoma Primario De Angulo Abierto, Rev Cubana Oftalmol, 2002, 35-39 (English Abstract), 15(1).
Curri, Joanne, Paragraph IV Letter to: Allergan, Inc. (Irvine, CA), Dec. 23, 2011, 12 Pages, Hi-Tech Pharmacal Co., Inc., Amityville, NY.
Data Sheet for Brimonidine, 2007, 1 Page.
Data Sheet for Timolol, 2007, 1 Page.
David Duplay, Physicians' Desk Reference, Physicians' Desk Reference, 2004, 553-554, 58th.

(56) References Cited

OTHER PUBLICATIONS

David, Robert et al, Brimonidine in the Prevention of Intraocular Pressure Elevation Following Argon Laser Trabeculoplast, Arch. Opthalmol., Oct. 1993, 1387-1390, 111(10).
Davies, Sean, Hydrolysis of Bimatoprost (Lumigan) to Its Free Acid By Ocular Tissue In Vitro, Journal of Ocular Pharmacology and Therapeutics, 2003, 45-54, 19(1).
De Clercq, P., Cyclopentanones-VXL., Prostaglandin Synthesis Involving Catalytic Hydrogenation of 2,3-Dialkyl-4-Hydroxy-2-Cyclopentenones, Tetrahedron, 1976, 2747-2752, 32.
Deardorff, Dwight, Ophthalmic Preparation, Remington's Pharmaceutical Sciences, 1975, 1488, 15th ed.
Debbasch, Caroline et al, Evaluation of the Toxicity of Benzalkonium chloride on the Ocular Surface, J. Tox. Cut & Ocul. Tox., 2000, 105-115, 19 (2&3).
Decision from the Opposition Division of the European Patent Office revoking European Patent EP1496912, dated Jul. 29, 2015, 32 pages.
Deluca, Patrick et al, Formulation of Small Volume Parenterals, Pharmaceutical Dosage Forms: Parenteral Medications, 1992, 173-248, 1.
Derick, Robert et al, Brimonidine Tartrate: A One-month Dose Response Study, Ophthalmology, 1997, 131, 104 (1).
Desai, Suketu, Ocular Drug Formulation and Delivery, Encyclopedia of Pharmaceutical Technology, 1995, 43-75, 11.
Diestelhorst, Michael et al, Comparison of Two Fixed Combinations of Latanoprost and Timolol in Open-Angle Glaucoma, Graege's Arch Clin Exp Ophthalmol, 1998, 577-581, 236.
Doyle, Williams et al, New Aqueous Inflow Inhibitors, Seminars in Ophthalmology, 1999, 159-163, 14(3).
Dubiner, Harvey, Efficacy and Safety of Bimatoprost in Patients With Elevated Intraocular Pressure: a 30-Day Comparison With Latanoprost, Surv. Ophthalmol, 2001, S353-S560, 45 (4).
Eisenberg, Dan, Bimatoprost and Travoprost: A Review of Recent Studies of Two New Glaucoma Drugs, Survey of Ophthalmology, 2002, S105-S115, 47 (1).
Elman, Michael, Age-related macular degeneration, Int. Ophthalmol. Clin., 1986, 117-144, 26(2).
EPO Correspondence, Decision of the Technical Board of Appeal 3.3.02 of Apr. 17, 2012, dated Apr. 25, 2012, 12 Pages.
Faulkner, Robert, Aqueous Humor Concentrations of Bimatoprost Free Acid, Bimatoprost and Travoprost Free Acid in Cataract Surgical Patients administered Multiple Topical Ocular Doses of LUMIGAN or TRAVATAN, Journal of Ocular Pharmacology and Therapeutics, 2010, 147-156, 26(2).
FDA Label For Approved NDA 22-184 of Lumigan 0.01% and Lumigan 0.03%, Aug. 31, 2010.
Fechtner, Realini et al, Fixed combinations of topical glaucoma medications, Curr. Opin. Ophthalmol., 2004, 132-135, 15(2).
Fechtner, Robert et al, The Future of Glaucoma Diagnosis and Therapy, The Future of Glaucoma Diagnosis and Therapy, 2000, 419-426.
Feldman, Edward, Laser Treatment of Subretinal Neovascularization, Int. Ophthalmol. Clin., 1986, 15-174, 26(2).
Frenkel, R E et al, Evaluation of Circadian Control of Intraocular Pressure After a Single Drop of Bimatoprost 0.03% or Travoprost 0.004%, Curr. Med. Res. Opin., Apr. 2008, 919-923, 24(4).
Frishman, William et al, Cardiovascular Considerations in Using Topical, Oral, and Intravenous Drugs for the Treatment of Glaucoma and Ocular Hypertension—Focus on µ-Adrenergic Blockade, Heart Disease: A Journal of Cardiovascular Medicine, 2001, 386-397, 3(6).
Front and date-stamped (Apr. 11, 2001) pages of Archives of Ophthalmology, vol. 119, retrieved from hardcopy of journal issue at New York Academy of Medicine Librar.
Gabelt, B'Ann et al, Apraclonidine and Brimonidine Effects on Anterior Ocular and Cardiovascular Physiology in Normal and Sympathectomized Monkeys, Exp. Eye. Res., 1994, 633-644, 59.
Gandolfi, Stefano, Three-month Comparison of Bimatoprost and Latanoprost in Patients With Glaucoma and Ocular Hypertension, Adv. Ther., 2001, 110-121, 18.
Gasset, Antonio et al, Benzalkonium Chloride Toxicity to the Human Cornea, American Journal of Ophthalmology, Aug. 1977, 169-171, 84(2).
Giuffre, Giuseppe, The Effects of Prostaglandin F2α in the Human Eye, Graefe's Archive Clin. & Exper. Ophthal., 1985, 139-141, 222.
Goni, Francisco et al, Comparison of Fixed-Combination Brimonidine and Timolol with Concomitant Use of the Individual Components in Glaucoma and Ocular Hypertension: Achievement of Clinically Relevant IOP Reductions, 5th International Glaucoma Symposium (IGS), Mar. 2005, 3 pages.
Goni, Francisco, 12-week study comparing the fixed combination of brimonidine and Timolol with concomitant use of the individual components in patients with glaucoma and ocular hypertension, European Journal of Ophthalmology, 2005, 581-590, 15(5).
Grass, George, Mechanisms of Corneal Drug Penetration I: In Vivo and In Vitro Kinetics, Journal of Pharmaceutical Sciences, Jan. 1988, 3-14, 77 (1).
Green, Keith, Influence of Various Agents on Corneal Permeability, American Journal of Ophthalmology, 1971, 897-905, 72.
Green, Keith, Prednisolone Phosphate Penetration Into and Through the Cornea, Investigative Ophthalmology, 1974, 316-319, 13 (4).
Green, Keith, The Effects of Preservatives on Corneal Permeability of Drugs, Biopharmaceutics of Ocular Drug Delivery, 1993, 43-59.
Gurwitz, Jerry et al, Treatment for Glaucoma: Adherence by the Elderly, Am. J. Public Health, 1993, 711-716, 83(5).
Guttman, Cheryl et al, Study Dispels Myths on Costs of Glaucoma Therapy, Managed Healthcare, Jul. 2000, 37-38.
Handbook of Pharmaceutical Excipients, Monographs for Water, Sodium Phosphate, Sodium Chloride, and Citric Acid Monohydrate (1994).
Hecht, Gerald, Chapter 89: Ophthalmic Preparations, Remington: The Science and Practice of Pharmacy, 1995, 1563-1576, 2.
Hecht, Gerald, Ophthalmic Preparations, Remington: The Science and Practice of Pharmacy, 2000, 819-835, 20 edition.
Hellberg, Mark et al, The Hydrolysis of the Prostaglandin Analog Prodrug Bimatoprost to 17-Phenyltrinor by PGF2α Human and Rabbit Ocular Tissue, J. Ocular Pharmacol. Ther., 2003, 97-103, 19(2).
Herrin, Stan, What's New in Ophthalmic Drugs, Review of Ophthalmology, Jan. 1998, 77-81.
Hi-Tech Pharmacal, "Letter regarding abbreviated new drug application," Apr. 22, 2009.
Higaki, Kazutaka et al, Estimation And Enhancement Of In Vitro Corneal Transport Of S-1033, A Novel Antiglaucoma Medication, International Journal Of Pharmaceutics, 1996, 165-173, 132, Elsevier, US.
Ho, Norman et al, Physical Model Approach to the Design of Drugs with Improved Intestinal Absorption, Design Of Biopharmaceutical Properties Through Prodrugs & Analogs, 1977, 136-227, Edward B. Roche ed.
Hodges, Norman, Preservative Testing, 13 Encyclopedia of Pharmaceutical Technology, 1996, 21-37, 13.
Hommer, A.B. et al, Efficacy and Safety of Unoprostone, Dorzolamide, and Brimonidine and Adjunctive Therapy to Timolol in Patients with primary open-angle glaucoma and ocular hypertension, Investigative Ophthalmology & Visual Science, Mar. 15, 2001, S554, 42(4).
Honohan, Thomas, Duration of Activity of the Acid, Methyl Ester and Amide of an Orally Active Platelet Aggregation Inhibitory Prostanoid in the Rat, Prostaglandins, 1980, 139, 19.
Hoyng, Philip et al., Pharmacological Therapy For Glaucoma, Drugs, 2000, 411-434, 59(3), US.
Huang, Andrew et al, Paracellular Permeability of Corneal and Conjunctival Epithelia, Investigative Ophthalmology & Visual Science, 1989, 684-689, 30(4).
Hutzelmann, Jill et al, Comparison of the Safety and Efficacy of the Fixed Combination of Dorzolamide/Timolol and the Concomitant Administration of Dorzolamide and Timolol: A Clinical Equivalence Study, Br J Ophthalmol, 1998, 1249-1253, 82.

(56) References Cited

OTHER PUBLICATIONS

Information on Alphagan® in the Physician's Desk Reference, 54th Ed. (2000).
Information on Alphagan® in the Physician's Desk Reference, 55th Ed. (2001).
Information on Alphagan® in the Physician's Desk Reference, 56th Ed. (2002).
Information on Cosopt® in the Physician's Desk Reference, 53rd Ed. (1999).
Information on Cosopt® in the Physician's Desk Reference, 55th Ed. (2001).
Information on Cosopt® in the Physician's Desk Reference, 56th Ed. (2002).
Information on Timoptic® in the Physician's Desk Reference, 54th Ed. (2000).
Information on Timoptic® in the Physician's Desk Reference, 55th Ed. (2001).
Information on Timoptic® in the Physician's Desk Reference, 56th Ed. (2002).
Ischemia, Dorland's Illustrated Medical Dictionary, 1988, 857, 27 ed, W.B. Sunders Company.
Jackson, A.L. et al, Cardiovascular effects of Timolol, Brimonidine and Brimonidine/Timolol in combination, Investigative Ophthalmology & Visual Science, 2001, S418, 42(4).
Jarvinen, Kristiina et al, Ocular Absorption Following Topical Delivery, Advanced Drug Delivery Reviews, 1995, 3-19, 16.
Jordan, B.A. et al, G-Protein-Coupled Receptor Heterodimerization Modulates Receptor Function, Nature, 697-700, Jun. 17, 1999, 399(6737).
Katz, Jay et al, Brimonidine Tartrate 0.2% Twice Daily vs Timolol 0.5% Twice Daily: 1-Year Results in Glaucoma Patients, Am. J. Ophth., 1999, 20-26, 127(1).
Katz, Jay et al, Comparison of Human Ocular Distribution of Bimatoprost and Latanoprost, Investigative Ophthalmology & Visual Science, Jul. 9, 2010, 1-28.
Katz, Jay, Twelve-Month, Randomized, Controlled Trial of Bimatoprost 0.01%, 0.0125%, and 0.03% in Patients with Glaucoma or Ocular Hypertension, Am J Ophthalmology, 2010, 661-671, 149(4).
Kaur, Indu Pal et al, Formulation and Evaluation of Ophthalmic Preparations of Acetazolamide, International Journal of Pharmaceutics, 2000, 119-127, 199.
Kaur, Indu Pal et al, Penetration Enhancer and Ocular Bioadhesives: Two New Avenues for Ophthalmic Drug Delivery, Drug Development and Industrial Pharmacy, 2002, 353-369, 28(4).
Keller, N. et al., Increased Corneal Permeability Induced by the Dual Effects of Transient Tear Film Acidification and Exposure to Benzalkonium Chloride, Experimental Eye Research, 1980, 203-210, 30.
Kibbe, Arthur, Benzalkonium Chloride, Handbook of Pharmaceutical Excipients, 2000, 33-35.
Konstas, Anastasios et al, Brimonidine 0.2% Given Two or Three Times Daily Versus Timolol Maleate 0.5% in Primary Open Angle Glaucoma, Am. J. Ophthalmology, Jun. 2001, 729-733, 131(6).
Kuwayama, Y., Sympathetic Nerve α2 Stimulants, Drug Therapy of Glaucoma, 2001, 234-236(Translation), Department of Ophthalmology, Osaka Hospital of Welfare Pension.
Kuwayama, Y., Sympathetic Nerve α2 Stimulants, Drug Therapy of Glaucoma, 2001, 234-236, Department of Ophthalmology, Osaka Hospital of Welfare Pension.
L'Esperance, Francis, Department of Ophthalmology, 1989, 989-991, 3rd ed.
Laibovitz, Robert, Comparison of the Ocular Hypotensive Lipid AGN 192024 With Timolol, Arch Ophthal, 2001, 994, 119.
Larsson, Lil-Inger, Aqueous Humor flow In Normal Human Eyes Treated With Brimonidine And Timolol, Alone And In Combination, Archives Of Opthalmology, 2001, 492-495, 119, US.
Larsson, Lil-Inger, The Effect on Diurnal Intraocular Pressure of the Fixed Combination of Latanoprost 0.005% and Timolol 0.5% in Patients With Ocular Hypertension, Acta Ophthalmol. Scand., 2001, 125-128, 79.
Lawrence, C.A., An Evaluation of Chemical Preservatives for Ophthalmic Solutions, J Am Pharm Assoc, 1955, 457, 44(8).
Lawrence, C.A., Chemical Preservatives for Ophthalmic Solutions, Am J Ophthal, 1955, 385, 39.
Leblanc, Raymond, Twelve-Month Results of an Ongoing Randomized Trial Comparing Brimonidine Tartrate 0.2 % and Timolol 0.5 % with Glaucoma or Ocular Hypertension, Ophthalmology, Oct. 1998, 1960-1967, 105(10).
Lee, David A. et al, Emerging Perspectives on Glaucoma: highlights of a roundtable discussion, American Journal of Ophthalmology, Oct. 1, 2000, at p. S8, S1-11.
Lee, David et al, The Effectiveness and Safety of Brimonidine as Mono-, Combination, or Replacement Therapy for Patients with Primary Open-Angle Glaucoma or Ocular Hypertension: A Post Hoc Analysis of an Open-Label Community Trial, Journal of Ocular Pharmacology and Therapeutics, 2000, 3-18, 16(1).
Lee, Vincent et al, Improved Ocular Drug Delivery with Prodrugs, Prodrugs: Topical and Ocular Drug Delivery, 1992, 221-297, Kenneth Sloan Edition.
Lee, Vincent et al, Review: Topical Ocular Drug Delivery: Recent Developments and Future Challenges, Journal of Ocular Pharmacology, 1986, 67-108, 2(1).
Li, Zong-Yi et al, Apoptosis in Retinitis Pigmentosa, Degenerative Disease of the Retina, 1995, 1-8.
Liang, Y. et al, Identification and Pharmacological Characterization of the Prostaglandin FP Receptor and FP Receptor Variant Complexes, Br. J. Pharmacol., 2008, 1079-1093, 154.
Lumigan® 0,1 mg/ml, 3 pages, Jan. 2010.
Lumigan® RC (Allergan) (Bimatoprost Ophthalmic Solution 0.01%), 2009, 7 Pages.
Lumigan, Product Description, Allergan, Inc., Jul. 2003, pp. 1-6.
LUMIGAN® monograph in the 57th PDR (2003).
Lyle, Donald, Early Ocular Manifestations in the Laurence-Moon-Biedl Syndrome, American Journal of Ophthalmology, 1946, 939-946, 29.
Maclure, G.M. et al, Effect on the 24-Hour Diurnal Curve of Intraocular Pressure on a Fixed Ration Combination of Timolol 0.5% and Pilocarpine 2% in Patients With COAG Not Controlled on Timolol 0.5%, British Journal of Ophthalmology, 1989, 827-831, 73.
Madhu, Cherukury et al, Effect of Benzalkonium Chloride/EDTA on the Ocular Bioavailability of Ketorolac Tromethamine Following Ocular Instillation to Normal and De-epithelialized Corneas of Rabbits, Journal of Pharmaceutical Sciences, Apr. 1996, 415-418, 85(4).
Malhotra, Manjusha et al, Permeation Through Cornea, Indian Journal of Experimental Biology, Jan. 2001, 11-24, 39.
Martin, F.N., Preparation of Ophthalmic Solutions With Special Reference to Hydrogen Ion Concentration and Tonicity, Arch Ophthal, 1950, 561, 44.
Martinez, Antonio et al., Efficacy And Safety Of Bimatoprost/Timolol Fixed Combination In The Treatment Of Glaucoma Or Ocular Hypertension, Expert Opinion Pharmacotherapy, Jan. 1, 2008, 137-143, 9 (1).
Maurice, David, The Effect of the Low Blink Rate in Rabbits on Topical Drug Penetration, J Ocular Pharmacology and Therapeutics, 1995, 297-304, 11(3).
Maus, Todd et al, Comparison of the Early Effects of Brimonidine and Apraclonidine as Topical Ocular Hypotensive Agents, Arch. Ophthalmol., 1999, 586, 117.
Maxey, Kirk, The Hydrolysis of Bimatoprost in Corneal Tissue Generates a Potent Prostanoid FP Receptor Agonist, Survey of Ophthalmology, Aug. 2002, S34-S40, 47 (Supp. 1).
McKinnon, S.J., Glaucoma, apoptosis, and neuroprotection, Curr. Opin. Ophthalmol., Apr. 1997, 28-37, 8(2).
McPherson, Samuel, Self-Sterilizing Ophthalmic Solutions, Am J Ophthal, 1949, 675, 32.
Mealy, N.E., Ophthalmic Drugs, Drugs of the Future, 2002, 509-523, 27 (5).

(56) References Cited

OTHER PUBLICATIONS

Medical Review, Application No. 21-275, Center for Drug Evaluation and Research, 2001.
Melamed, Sholomo et al, Ongoing Clinical Assessment of the Safety Profile and Efficacy of Brimonidine Compared with Timolol: Year-Three Results, Clin. Ther., 2000, 103-110, 22(1).
Merck & Co., Inc. "Cosopt® (dorzolamide hydrochloride-timolol maleate ophthalmic solution) data sheet"; NDA 20-869/S-034; Jul. 2008.
Merck & Co., Inc. "TRUSOPT® (Dorzolamide Hydrochloride Ophthalmic Solution) data sheet," NDA 20-408/S-033; Jul. 1997.
Meszaros, Elizabeth, New Pharmacotherapy Approaches Improve Focus of Glaucoma Treatment, Managed Healthcare, Jan. 1998, 44-46.
Miller, William et al, Biological Activities of 17-Phenyl-18, 19,20-Trinorprostaglandins, Prostaglandins, Jan. 1975, 9-18, 9(1).
Mitra, Ashim, Ophthalmic Drug Delivery Systems, Drugs and the Pharmaceutical Sciences, 2003, 6 Pages, 2nd Edition (vol. 130).
Morrison, John et al, Adjunctive Glaucoma Therapy: A Comparison of Apraclonidine to Dipivefrin When Added to Timolol Maleate, Ophthalmology, 1989, 3-7, 96.
Muchnick, Bruce et al, The Optic Nerve in Glaucoma, The Optic Nerve in Clinical Practice, 1997, 103-115.
Mullen, William, Ophthalmic Preservatives and Vehicles, Surv Ophthal, 1973, 469, 17(6).
Munk, S.A. et al., Analogs of UK 14,304: Structural Features Responsible for Alpla2 Adrenoceptor Activity, Bioorganic and Medicinal Chemistry Letters, 1995, 1745-1750, vol. 5, No. 15, Elsevier Science Ltd.
Nagasubramanian, S., A Comparison of the Ocular Hypotensive Efficacy, Safety and Acceptability of Brimonidine 0.2% Twice Daily versus Pilocarpine 2.0% Thrice Daily as Adjunct Therapy wit Beta-Blockers, Glaucoma Update IV, 2000, 203-208.
Nema, Sandeep et al, Excipients—Their Role in Parenteral Dosage Forms, Encyclopedia of Pharmaceutical Technology, 2002, 1164-1187, 2.
Netland, Peter et al, Brimonidine Purite And Brimatoprost Compared With Timolol And Latanoprost In Patients With Glaucoma And Ocular Hypertension, Advances in Therapy, 2003, 20-30, 20 (1).
Neufeld, Arthur, New Conceptual Approaches for Pharmacological Neuroprotection in Glaucomatous Neuronal Degeneration, J. Glaucoma, Dec. 1996, 434-438, 7(6).
Nilsson, SIV, PGF 2α Increases Uveoscleral Outflow, Invest. Ophthalmol. Vis. Sci, 1987, 284-285, 28 (Suppl).
Nixon, Donald et al., Three-Month, Randomized, Parallel-Group Comparison Of Brimonidine-Timolol Versus Dorzolamide-Timolol Fixed-Combination Therapy, Current Medical Research And Opinion, Apr. 24, 2009, 1645-1653, 25 (7).
Noecker, Robert et al, Corneal and Conjunctival Changes Caused by Commonly Used Glaucoma Medications, Cornea, 2004, 490-496, 23.
Noecker, Robert, Bimatoprost/Latanoprost Study Group. A Six Month Randomized Clinical Trial Comparing The Intraocular Pressure Lowering Efficacy of Bimatoprost and Latanoprost in Patients With Ocular Hypertension or Glaucoma, Am J Ophthal, 2003, 55-63, 135.
Noecker, Robert, Effects of Common Ophthalmic Preservatives on Ocular Health, Advances in Therapy, Sep.-Oct. 2001, 205-215, 18(5).
Nordlund, J.R. et al, Cardiovascular, Pulmonary and Ocular Hypotensive Effects of 0.2% Brimonidine, Arch. Opthalmol., Jan. 1995, 77-83, 113.
Novack, Gary et al, Commercially Available Ocular Hypotensive Products: Preservative Concentration, Stability, and Storage, In-Life Utilization, Journal of Glaucoma, 2001, 483-486, 10.
O'Brien, C.S., Carbaminoyl-choline Chloride in the Treatment of Glaucoma Simplex, Arch Ophthal, 1942, 253, 27.
O'Brien, C.S., Doryl in the Treatment of Glaucoma Simplex, Tran Am Ophthal Soc, 1941, 175, 39.
Ogundele, Abayomi et al, Impact of Topical Bimatoprost 0.01% and Bimatoprost 0.03% on Conjunctival Irritation in Rabbits, Clinical Ophthalmology, Feb. 13, 2010, 77-80, 4.
Ogundele, Abayomi et al, In Vivo Comparative Study of Ocular Vasodilation, A Relative Indicator of Hyperemia, in Guinea Pigs Following Treatment With Bimatoprost Ophthalmic Solutions 0.01% and 0.03%, Clinical Ophthalmology, Jun. 19, 2010, 649-652, 4.
Okabe, Komei et al, Effect of Benzalkonium Chloride On Transscleral Drug Delivery, Investigative Ophthalmology & Visual Science, 2005, 703-708, 46.
Ormrod, Douglas et al, Topical Dorzolamide 2%/Timolol 0.5%, Drugs and Aging, Dec. 2000, 477-496, 17(6).
Package Insert for Alphagen, Allergan, Inc., Dec. 20, 2001.
Package Insert for Timoptic, Merck & Co., Apr. 2000.
Package Insert for Timoptic, Merck & Co., Apr. 2001.
Package Insert for Timoptic, Merck & Co., Sep. 2005.
Parrish, Richard, A Comparison of Latanoprost, Bimatoprost, and Travoprost In Patients With Elevated Intraocular Pressure: A 12-Week, Randomized, Masked Evaluator Multicenter Study, Am J Ophthalmol, 2003, 688-703, 135.
Patient Information brochure, "Brimonidine," www.ausdi.com, 2000.
Pfeiffer, N, New Developments in Glaucoma Drug Therapy, Ophthalmologist, 1992, W1-W13, 89.
Pfister, Roswell, The Effects of Ophthalmic Drugs, Vehicles, and Preservatives on Corneal Epithelium: a Scanning Electron Microscope Study, Effects of Opthalmic Drugs, 1976, 246-259, 15 (4).
Pharmacia & Upjohn, Xalatan (Latanoprost Ophthalmic Solution), 1998, 2 Pages.
Pharmacia Launches Dual Glaucoma Therapy, Manufacturing Chemist, Nov. 2001, 6, 72(11).
Physicians Desk Reference, Information on Alphagan® in the Physician's Desk Reference, 52nd Ed., Physicians Desk Reference 52 Edition 1998, Jan. 1, 1998, 3 Pages, 52 edition, 1998, Medical Economics Company, US.
Physicians' Desk Reference, 56th ed., pp. 212-13, 543, 553-54, 2864-65 (2002).
Physicians' Desk Reference, 59th ed., pp. 555-56 (2005).
Pisella, Pierre-Jean, Conjunctival Proinflammatory and Proapoptotic Effects of Latanoprost and Preserved and Unpreserved Timolol: An Ex Vivo and In Vitro Study, Investigative Ophthalmology & Visual Science, 2004, 1360-1368, 45.
Podder, Samir, Improving the Safety of Topically Applied Timolol in the Pigmented Rabbit Through Manipulation of Formulation Composition, Exp. Eye Res., 1992, 747-757, 54.
Poyer, J.F. et al, Prostaglandin F2α Effects on Isolated Rhesus Monkey Ciliary Muscle, Invest. Ophthalmol. Vis. Sci., Nov. 1995, 2461-2465, 36(12).
Prescribing information for TIMOPTIC in the Physician's Desk Reference,("TIMOPTIC PDR"), Physicians' Desk Reference 52 Edition, Jan. 1, 1998, 6 Pages.
Quigley, Harry et al, Retinal Ganglion Cell Death in Experimental Glaucoma and After Axotomy Occurs by Apoptosis, Invest. Ophth. Vis. Sci., 1995, 774-786, 36.
Raymond Rowe et al, Handbook of Pharmaceutical Excipients, APha Publications, 2003, 2 pages, 4th edition.
Remington, The Science and Practice of Pharmacy, 20th ed. at 831 (2000).
Remington, The Science and Practice of Pharmacy, 21st ed. at 864 (2005).
Remington's Pharmaceutical Sciences 1501 (15th ed. 1975).
Resul, B et al, Phenyl-substituted Prostaglandins: Potent and Selective Antiglaucoma Agents, J. Med. Chem., Jan. 22, 1993, 243-248, 36(2).
Robin, Alan et al, An Accurate Comparison of Bimatoprost's Efficacy and Adverse Effects, Arch Ophthalmol, Jul. 2002, 999-1000, 120.
Roggeband, R., Eye Irritation in Rabbit and Man After Single Applications of Equal Volumes of Undiluted Model Liquid Detergent Products, Food & Chem Toxic, 2000, 727, 38.
Romano, Maria Rosaria et al, Evidence for the Involvement of Cannabinoid DB1 Receptors in the Bimatoprost-Induced Contrac-

(56) References Cited

OTHER PUBLICATIONS tions on the Human Isolated Ciliary Muscle, Investigative Ophthalmology & Visual Science, Aug. 2007, 3677-3382, 48(8).
Rosenthal, A.L. et al, A Comparison of the Safety and Efficacy of Brimonidine 0.2% BID Versus TID, in Subjects with Elevated Intraocular Pressure, Invest. Ophth. Vis. Sci., 1996, S1102, 37(3).
Rote Liste 2001: Arzneimittelverzeichnis Fur Deutschland, 2001, 16 Pages.
Sall, K.N. et al, A Comparison of the Ocular Hypotensive Effect of Dorzolaminde Hydrochloride/Timolol Maleate to that of the Concomitant Therapy with Brimonidine Tartate and Timolol Maleate in Patients with Ocular Hypertension or Primary open-Angle Glaucoma, Investigative Ophthalmology & Visual Science, 2001, S822, 4412-6431, 42(4).
Sall, Kenneth et al, Dorzolamide/Timolol Combination Versus Concomitant Administration of Brimonidine and Timolol—Six-Month Comparison of Efficacy and Tolerability, Ophthalmology, 2003, 615-624, 110.
Sasaki, Hitoshi et al, Different Effects of Absorption Promoters on Corneal and Conjunctival Penetration of Ophthalmic Beta-Blockers, Pharmaceutical Research, 1995, 1146-1150, 12(8).
Sasaki, Hitoshi et al, Enhancement of Ocular Drug Penetration, Critical Reviews in Therapeutic Drug Carrier Systems, 1999, 85-146, 16(1).
Sasaki, Hitoshi et al, Ophthalmic Preservatives As Absorption Promoters For Ocular Drug Delivery, J. Pharm. Pharmacol., 1995, 703-707, 47, US.
Sasaki, Hitoshi, Modification of Ocular Permeability of Peptide Drugs by Absorption Promoters, Biol Pharm Bull, 2000, 1524, 23(12).
Sasaki, Hitoshi, Ocular Permeability of FITC-Dextran with Absorption Promoter for Ocular Delivery of Peptide Drug, J Drug Target, 1995, 129, 3.
Scholz, Martina, Pilocarpine Permeability Across Ocular Tissues and Cell Cultures: Influence of Formulation Parameters, Journal of Ocular Pharmacology and Therapeutics, 2002, 455-468, 18 (5).
Schuman, Joel et al, A 1-Year Study of Brimonidine Twice Daily in Glaucoma and Ocular Hypertension, Arch. Ophthalmol., 1997, 847-852, 115.
Schuman, Joel, Clinical Experience with Brimonidine 0.2% and Timolol 0.5% in Glaucoma and Ocular Hypertension, Survey of Opthalmology, Nov. 1996, S27-S37, 41, US.
Schuman, Joel, Effects of Systemic β-blocker Therapy on the Efficacy and Safety of Topical Brimonidine and Timolol, Ophthalmology, 2000, 1171-1177, 107(6).
Schumer, Robert A. et al, The Nerve Of Glaucoma!, Archives Of Opthalmology, Jan. 1994, 37-44, 112, US.
Schumer, Robert et al, Medical Treatment of Glaucoma, Current Opinion in Ophthalmology, 1991, 140-150, 2.
Schwartz, Bernand, Circulatory Defects of the Optic Disk and Retina in Ocular Hypertension and High Pressure Open-Angle Glaucoma, Surv. Ophthalmol., 1994, S23-S34, 38.
Serle, Janet B. et al, Selective α2-Adrenergic Agonists B-HT 920 and UK14304-18, Arch Ophthalmol, Aug. 1991, 1158-1162, 109.
Serle, Janet B., Pharmacological Advances in The Treatment Of Glaucoma, Drugs & Aging, 1994, 156-170, 5 (3), US.
Serle, Janet, A Comparison of the Safety and Efficacy of Twice Daily Brimonidine 0.2% Versus Betaxolol 0.25% in Subjects with Elevated Intraocular Pressure, Surv. Ophth., 1996, S39-S47, 41 (Suppl. 1).
Sharif, N.A. et al, Cat Iris Sphincter Smooth-Muscle Contraction: Comparison of FP-Class Prostaglandin Analog Agonist Activities, J. Ocul. Pharmacol. Ther., Apr. 2008, 152-163, 24(2).
Sharif, N.A. et al, Human Ciliary Muscle Cell Responses to FP-class Prostaglandin Analogs: Phosphoinositide Hydrolysis, Intracellular Ca2+ Mobilization and Map Kinase Activation, J. Ocul. Pharmacol Ther., 2003, 437-455, 19.

Sharif, N.A. et al, Human Trabecular Meshwork cell Responses Induced by Bimatoprost, Travoprost, Unoprostone, and Other FP Prostaglandin Receptor Agonist Analogues, Invest. Ophthalmol Vis. Sci., 2003, 715-721, 44.
Sharif, N.A. et al, Ocular Hypotensive FP Prostaglandin (PG) Analogs: PG Receptor Subtype Binding Affinities and Selectivities, and Agonist Potencies at FP and Other PG Receptors in Cultured Cells, Journal of Ocular Pharmacology and Therapeutics, 2003, 501-515, 19(6).
Sharif, N.A. et al, Update and Commentary on the Pro-Drug Bimatoprost and a Putative Prostamide Receptor, Expert Rev. Ophthalmol., 2009, 477-489, 4(5).
Sherwood, Mark et al, Six-Month Comparison of Bimatoprost Once-Daily and Twice-Daily with Timolol Twice-Daily in Patients Dailywith Elevated Intraocular Pressure, Survey of Ophthalmology, 2001, S361-S368, 45(4).
Sherwood, Mark et al, Twice-Daily 0.2% Brimonidine-0.5% Timolol Fixed-Combination Therapy vs Monotherapy With Timolol or Brimonidine in Patients With Glaucoma or Ocular Hypertension, Arch Ophthalmol, 2006, 1230-1238, 124.
Shin, Dong et al, Long-Term Brimonidine Therapy in Glaucoma Patients With Apraclonidine Allergy, Am J Ophthalmol, 1999, 511-515, 127.
Silvestre, J.F. et al, Allergic Contact Dermatitis From Apraclonidine in Eyedrops, Contact Dermatitis, 2001, 251, 45.
Simmons, Steven et al, Comparison of Brimonidine with Latanoprost in the Adjunctive Treatment of Glaucoma, Clin. Ther., 2000, 388-399, 22(4).
Simmons, Steven et al, Three-month Comparison of Brimonidine and Latanoprost as Adjunctive Therapy in Glaucoma and Ocular Hypertension Patients Uncontrolled on β-blockers: Tolerance and Peak Intraocular Pressure Lowering, Ophthalmology, 2002, 307-314, 109(2).
Simmons, Steven, Efficacy of Brimonidine 0.2% and Dorzolamide 0.2% as Adjunctive Therapy to Beta-Blockers in Adult Patients with Glaucoma or Ocular Hypertension, Clin. Therapeutics, 2001, 604-619, 23(4).
Sjoquist, Birgitta et al, Ocular and Systemic Pharmacokinetics of Latanoprost in Humans, Surv. Ophthalmol., Aug. 2002, S6-S12, 47(Suppl 1).
Sjoquist, Birgitta et al, Pharmacokinetics of Latanoprost in the Cynomolgus Monkey. 3rd Communication: Tissue Distribution After Topical Administration on the Eye Studied by Whole Body Autoradiography, Glaucoma Research Laboratories. Arzneim-Forsch/Drug Res., 1999, 240-249, 49.
Skolaut, Milton, Ophthalmic Medication, Bull Am Soc Hosp Pharm, 1948, 172, 5(4).
Soderstrom, M.B. et al, Timolol-Pilocarpine Combined vs. Timolol and Pilocarpine Given Separately, Am. J. Ophthalmology, 1989, 465-470, 107.
Spada, C.S. et al, Bimatoprost and Prostaglandin F2α Selectively Stimulate Intracellular Calcium Signaling in Different Cat Iris Sphincter Cells, Exp. Eye Res., Jan. 2005, 135-145, 80(1).
Spaeth, George et al, The effects of brimonidine tartrate on the incidence of intraocular pressure (IOP) spikes following argon laser trabeculoplasty, Investigative Ophthalmology & Visual Science, 1992, 1159, 33(4).
Stamer, W.D. et al, Cellular Basis for Bimatoprost Effects on Human Conventional Outflow, Invest. Ophthalmol. Vis. Sci., Oct. 2010, 5176-5181, 51(10).
Stamper, Robert, Primary Drug Treatment for Glaucoma: Beta-Blockers Versus Other Medications, Survey of Ophthalmology, Jan.-Feb. 2002, 63-67, 47(1).
Starr, Michael, Further Studies on the Effects of Prostaglandin on Intraocular Pressure in the Rabbit, Experimental Eye Research, 1971, 170-177, 11.
Stern, F.A., Comparison of the Hypotensive and Other Ocular Effects of Prostaglandins E2 and F2α on Cat and Rhesus Monkey Eyes, Invest Ophthal Visual Sci, 1982, 588-598, 22.
Stewart, W.C. et al, Comparison of the Efficacy and Safety of Latanoprost 0.0005% Compared to Brimonidine 0.2% or Dorzolamide 2% When Added to a Topical β-Adrenergic Blocker in

(56) References Cited

OTHER PUBLICATIONS

Patients with Primary Open-Angle Glaucoma or Ocular Hypertension, J. Ocu. Pharmacology and Therapeutics., 2000, 251-260, 16(3).
Stewart, William C., Perspectives In The Medical Treatment Of Glaucoma, Current Opinion In Opthalmology, Apr. 1999, 99-108, 10 (2), US.
Stewart, William et al, Cardiovascular Effects of Timolol Maleate, Brimonidine or Brimonidine/Timolol Maleate in Concomitant Therapy, Acta Ophthalmol Scand., Jun. 2002, 277-281, 80(3).
Stewart, William, Chronic Open-Angle Glaucoma and Lifestyle, Progress in Retinal and Eye Research, 1997, 16(4) 567-590,.
Stewart, William, Corneal Punctate Staining with Latanoprost, Bimatoprost, and Travoprost in Healthy Subjects, J Glaucoma, 2003, 475-479, 12 (6).
Stjernschantz, Johan et al, From PGF2α-isopropyl Ester to Latanoprost: A Review of the Development of Xalatan: The Proctor Lecture, Invest. Ophthalmol. Vis. Sci., May 2001, 1134-1145, 42(6).
Stjernschantz, Johan, Studies on Ocular Inflammation and Development of a Prostaglandin Analogue for Glaucoma Treatment, Exp. Eye Res., Apr. 2004, 759-766, 78(4).
Strohmaier, Kim et al, The Efficacy and Safety of the Dorzolamide-Timolol Combination Versus the Concomitant Administration of its Components, American Journal of Ophthalmology, Oct. 1998, 1936-1944, 105.
Sverrisson, T. et al, The Dorzolamide/Timolol Combination Versus Timolol Plus Pilocarpine: Patient Preference and Impact on Daily Life, J. Glaucoma, Oct. 1999, 315-324, 8(5).
Swan, Kenneth, Reactivity of the Ocular Tissues to Wetting Agents, American Journal of Ophthalmology, 1944, 1118-1122, 27.
Tang-Liu, Diane, Effects of Four Penetration Enhancers on Corneal Permeability of Drugs in Vitro, Journal of Pharmaceutical Sciences, 1994, 85-90, 83 (1).
Thygesen, J., Short-term Effect of Latanoprost and Timolol Eye Drops on Tear Fluid and the Ocular Surface in Patients with Primary Open-Angle Glaucoma and Ocular Hypertension, Acta Ophthal Scand, 2000, 37-41, 78.
Timmermans et al, Structure-Activity Relationships in Clonidine-Like Imidazolidines and Related Compounds, Progress in Pharmacology, 1980, 21-41, 3(1).
Tonjum, Asbjorn, Permeability of Rabbit Corneal Epithelium to Horseradish Peroxidase After the Influence of Benzalkonium Chloride, Acta Ophthalmologica, Jan. 22, 1975, 335-347, 53.
Toris, C.B. et al, Effects of Brimonidine on Aqueous Humor Dynamics in Human Eyes, Arch Ophthalmol., Dec. 1995, 1514-1517, 113.
Toyoda, K., Drugs for Use in Ophthalmology, Journal of Medicinal Drugs, 2002, 324-328(Translated), 38.
Toyoda, K., Drugs for Use in Ophthalmology, Journal of Medicinal Drugs, 2002, 324-328, 38.
Travatan (travoprost ophthalmic solution) 0.004% Product Insert, NDA 21-257, Mar. 16, 2001, 7 Pages.
Traverso, C.E. et al, Additivity of Brimonidine 0.2% BID or Pilocarpine 2.0% TID to Beta-Blocker Monotherapy, ARVO Annual Meeting Fort Lauderdale, Florida, Invest. Ophth. Vis. Sci., Mar. 1998, S480, 39(4).
Van Alphen, G.W.H.M. et al, The effect of Prostaglandins on the Isolated Internal Muscles of the Mammalian Eye, Including Man, Documenta Ophthalmologica, 1977, 397-415, 42(4).
Van Der Bijl, Pieter, Effects of Three Penetration Enhancers on Transcorneal Permeation of Cyclosporine, Cornea, 2001, 505-508, 20 (5).
Vielhauer, G.A. et al, Cloning and Localization of hFP(S): a Six-Transmembrane mRNA Splice Variant of the Human FP Prostanoid Receptor, Arch Biochem Biophys., Jan. 15, 2004, 175-185, 421(2).
Walter, Modell, Pharmacologic Action of Some Ophthalmic Drugs, Arch Ophthal, 1947, 160, 37.
Walter, Thomas, 24-Hour IOP Control with Once-daily Bimatoprost, Timolol Gel-forming Solution, or Latanoprost: A 1-Month, Randomized, Comparative Clinical Trial, Survey of Ophthalmology, 2004, S26-S35, 49(1).
Walters, T.R. et al, A pilot study of the efficacy and safety of AGN 190342-LF 0.02% and 0.08% in patients with elevated intraocular pressure, Arvo 1991 Annual Meeting Abstract Issue, Invest. Ophthalmol. Vis. Sci., 1991, 988, 32.
Walters, Tom, Development and Use of Brimonidine in Treating Acute and Chronic Elevations of Intraocular Pressure: A Review of Safety, Efficacy, Dose Response, and Dosing Studies, Surv. Ophth., Nov. 1996, S27, 41 (Suppl. 1).
Wang, Rong-Fang et al, Comparison of the Ocular Hypotensive Effect Of Brimonidine, Dorzolamide, Latanoprost, Or Artificial Tears Added To Timolol In Glaucomatous Monkey Eyes, Journal Of Glaucoma, 2000, 458-462, 9, Lippincott Williams & Wilkins, US.
Web page at JAMA Opthalmology (publisher of former Archives of Ophthalmology) for Apr. 2001 issue of Archives of Ophthalmology, vol. 119.
White, J.H. et al, Heterodimerization is Required for the Formation of a Functional GABA(B) Receptor, Nature, Dec. 17, 1998, 679-682, 396(6712).
Wigginton, Stephen et al, Choosing Beta-Blockers for Initial Medical Therapy for Glaucoma, Sury Ophthalmol, Jan. 2002, 68-73, 47(1).
Wigginton, Stephen et al, Choosing Initial and Combination Medical Therapy for Glaucoma, Glaucoma Diagnosis and Management, Sep. 2000, 417-427, vol. 13, No. 3.
Wilson, S.J. et al, Dimerization of the Human Receptors for Prostacyclin and Thromboxane Facilitates Thromboxane Receptor-Mediated Camp Generation, J. Biol. Chem., Dec. 17, 2004, 53036-53047, 279(51).
Wong, Paul, Apoptosis, retinitis pigmentosa, and degeneration, Biochem Cell Biol., Dec. 1994, 489-498, 72(11-12).
Woodford, Roger, Penetration Enhancers and The Percutaneous Absorption of Drugs: An Update, J. Toxicol.—Cut & Ocular Toxicol., 1986, 167-177, 5(3).
Woodward, David et al, Bimatoprost Effects on Aqueous Humor Dynamics in Monkeys, J. Ophthalmol., 2010, 1-5, vol. 2010.
Woodward, David et al, Bimatoprost: a Novel Antiglaucoma Agent, Cardiovascular Drug Reviews, 2004, 103-120, 22(2).
Woodward, David et al, Identification of an antagonist that selectively blocks the activity of prostamides (prostaglandin-ethanolamides) in the feline iris, British Journal of Pharmacology, 2007, 342-352, 150.
Woodward, David et al, The Pharmacology of Bimatoprost (LumiganTM), Surv Ophthalmol, 2001, S337-S345, Suppl 4.
Xalatan® Eye Drops, Retrieval Date : Oct. 2, 2010, 3 pages, http://home.intekom.com/pharm/pharmaca/xalatan.html.
Xalatan® product information in the PDR 59th edition, p. 2762-2763/(2005).
Xu, Ke-Ping, Corneal Organ Culture Model for Assessing Epithelial Responses to Surfactants, Tox. Sci., 2000, 306, 58.
Yablonski, Michael et al, A Fluorophotometric Study of the Effect of Topical Timolol on Aqueous Humor Dynamics, Exp. Eye Res., 1978, 135-142, 27.
Yamaji, K. et al, Prostaglandins E1 and E2, but not F2α or Latanoprost, Inhibit Monkey Ciliary Muscle Contraction, Curr. Eye Res., Aug. 2005, 661-665, 30(8).
Young, Richard, Pathophysiology of Age-related Macular Degeneration, Surv. Ophthalmol., 1987, 291-306, 31(5).
Yuksel, Nursen et al, The Short-Term Effect of Adding Brimonidine 0.2% to Timolol Treatment in Patients with Open-Angle Glaucoma, Ophtalmologica, 1999, 228-233, 213(3).

COMPOSITIONS AND METHODS FOR LOWERING INTRAOCULAR PRESSURE

CROSS REFERENCE TO RELATED APPLICATION

This application is a continuation of U.S. patent application Ser. No. 14/147,302, filed Jan. 3, 2014, which is a continuation-in-part of U.S. patent application Ser. No. 13/698,182, filed Nov. 15, 2012, and now abandoned, which is a U.S. National Stage Application under 35 U.S.C. §371 of PCT Application No. PCT/US10/61563, filed Dec. 21, 2010, which claims priority to U.S. Provisional Application No. 61/361,749, filed Jul. 6, 2010 and U.S. Provisional Application No. 61/288,936, filed Dec. 22, 2009, the disclosures of which are hereby incorporated by reference in their entireties and serve as the basis of a priority and/or benefit claim for the present application.

FIELD

Embodiments disclosed herein provide compositions and methods that lower intraocular pressure. The compositions and methods disclosed herein include bimatoprost, brimonidine and timolol and combinations thereof and are particularly suited for patients who require maximum medical therapy for lowering intraocular pressure and for treatment of glaucoma.

BACKGROUND

Numerous disturbances or disorders of the eye lead to an increase in intraocular pressure (IOP). For example, post-surgical or post-laser trabeculectomy, ocular hypertensive episodes and glaucoma all can result in increased IOP.

On the basis of its etiology, glaucoma has been classified as primary or secondary. Primary glaucoma, also known as congenital glaucoma, can occur in the absence of other ocular conditions. The underlying causes of primary glaucoma are not known. It is known, however, that the increased IOP observed in primary glaucoma is due to the obstruction of aqueous humor flow out of the eye. In chronic open-angle primary glaucoma, the anterior chamber and its anatomic structures appear normal, but drainage of the aqueous humor is impeded. In acute or chronic angle-closure primary glaucoma, the anterior chamber is shallow, the filtration angle is narrowed, and the iris may obstruct the trabecular meshwork at the entrance of the canal of Schlemm. Dilation of the pupil may also push the root of the iris forward against the angle to produce pupillary block precipitating an acute attack. Additionally, eyes with narrow anterior chamber angles are predisposed to acute angle-closure glaucoma attacks of various degrees of severity.

Secondary glaucoma results from another pre-existing ocular disease such as, without limitation, uveitis, intraocular tumor, enlarged cataract, central retinal vein occlusion, trauma to the eye, operative procedures and intraocular hemorrhage. Accordingly, any interference with the outward flow of aqueous humor from the posterior chamber into the anterior chamber and subsequently, into the canal of Schlemm can lead to secondary glaucoma.

Considering all types of glaucoma together, this ocular disorder occurs in about 2% of all persons over the age of 40. Unfortunately, glaucoma can be asymptomatic for years before progressing to a rapid loss of vision.

In cases where surgery is not indicated, topical β-adrenoreceptor antagonists have traditionally been the drugs of choice for treating glaucoma. Certain eicosanoids and their derivatives have also been reported to possess ocular hypotensive activity, and have been recommended for use in glaucoma management. Eicosanoids and their derivatives include numerous biologically important compounds such as prostaglandins and their derivatives. While prostaglandins were earlier regarded as potent ocular hypertensives, evidence has accumulated that some prostaglandins are highly effective ocular hypotensive agents ideally suited for long-term medical management of glaucoma.

Prostaglandins can be described as derivatives of prostanoic acid which have the structural formula:

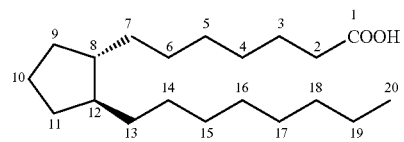

Particularly useful hypotensive prostaglandins include $PGF_{2\alpha}$, $PGF_{1\alpha}$, $PGE_{2\alpha}$, and certain lipid-soluble esters, such as $C_1$ to $C_5$ alkyl esters, e.g. 1-isopropyl ester, of such compounds. Many patients needing to lower their intraocular pressure are on fixed combination therapies such as COMBIGAN® and GANFORT®. However, for some patients, combination therapies are not enough to lower intraocular pressure and Triple Combination therapy is required. The combined effect is expected to result potentially in additional IOP reduction in patients with chronic open-angle glaucoma or ocular hypertension who are not well controlled on 2 IOP-lowering agents.

SUMMARY

Embodiments disclosed herein relate to enhanced medical therapy for patients with increased intraocular pressure (IOP) using a combination of IOP-lowering agents. Particularly, embodiments disclosed herein contain a Triple Combination of IOP-lowering agents for use by patients with increased IOP providing superior efficacy while maintaining safety and tolerability. In certain embodiments, the patient or subject is human.

Bimatoprost is a potent ocular hypotensive agent (Cantor, 2001; Sherwood et al, 2001). It is a synthetic prostamide, structurally related to prostaglandin F2α (PGF2α), that selectively mimics the effects of biosynthesized substances called prostamides.

Bimatoprost reduces IOP in humans by increasing aqueous humor outflow through the trabecular meshwork and enhancing uveoscleral outflow (Brubaker et al, 2001). Brimonidine tartrate is an alpha-2 adrenergic receptor agonist that is 1000-fold more selective for the alpha-2 adrenoceptor than the alpha-1 adrenoreceptor (Munk et al, 1994). It is thought that brimonidine tartrate lowers IOP by enhancing uveoscleral outflow and reducing aqueous humor formation (Report BIO-94-012; Serle et al, 1991). Timolol is a beta-1 and beta-2 non-selective adrenergic receptor blocking agent. Timolol lowers IOP by reducing aqueous humor formation (Coakes and Brubaker, 1978; Yablonski et al, 1978).

According to the various example embodiments, the compositions contain bimatoprost, brimonidine, and timolol. In another embodiment, the brimonidine is a salt thereof, such as brimonidine tartrate, and the timolol is a salt thereof, such as timolol maleate. In another embodiment, the compositions further contain sodium phosphate dibasic heptahydrate, citric acid monohydrate, sodium chloride, and sodium hydroxide in an aqueous carrier. In yet another embodiment, the compositions further contain benzalkonium chloride.

In another embodiment, the compositions contain 0.01% w/v bimatoprost, 0.15% w/v brimonidine tartrate, and 0.683% w/v timolol maleate. In this combination, both brimonidine tartrate and timolol maleate are at concentrations and regimens that are approved for the individual components. Bimatoprost in this combination, however, is at 0.01%, which is lower than the 0.03% concentration approved.

In yet another embodiment, the compositions further contain 1.5% w/v sodium phosphate dibasic heptahydrate, 0.025% w/v citric acid monohydrate, and 0.35% w/v sodium chloride. In yet another embodiment, the compositions further contain 0.005% w/v benzalkonium chloride.

In another embodiment, the compositions consist essentially of bimatoprost, brimonidine, and timolol. In another embodiment, the brimonidine is a salt thereof, such as brimonidine tartrate, and the timolol is a salt thereof, such as timolol maleate. In yet another embodiment, the compositions further consist essentially of sodium phosphate dibasic heptahydrate, citric acid monohydrate, sodium chloride, and sodium hydroxide in an aqueous carrier. In yet another embodiment, the compositions further consist essentially of benzalkonium chloride.

In another embodiment, the compositions consist essentially of 0.01% w/v bimatoprost, 0.15% w/v brimonidine tartrate, and 0.68% w/v timolol maleate. In another embodiment, the compositions further consist essentially of 1.5% w/v sodium phosphate dibasic heptahydrate, 0.025% w/v citric acid monohydrate, 0.35% w/v sodium chloride, sodium hydroxide, in an aqueous carrier. In yet another embodiment, the compositions further consists essentially of 0.005% w/v benzalkonium chloride.

In another embodiment, the compositions consist of bimatoprost, brimonidine, timolol, sodium phosphate dibasic heptahydrate, citric acid monohydrate, sodium chloride, and sodium hydroxide in an aqueous carrier. In another embodiment, the brimonidine is a salt thereof, brimonidine tartrate, and the timolol is a salt thereof, timolol maleate. In yet another embodiment, the compositions further consist of benzalkonium chloride.

In another embodiment, the compositions consist of 0.01% w/v bimatoprost, 0.15% w/v brimonidine tartrate, and 0.68% w/v timolol maleate, 1.5% w/v sodium phosphate dibasic heptahydrate, 0.025% w/v citric acid monohydrate, 0.35% w/v sodium chloride, sodium hydroxide, and water. In yet another embodiment, the compositions further consist of 0.005% w/v benzalkonium chloride.

In certain embodiments disclosed herein, the compositions do not contain, consist of, or consist essentially of components other than bimatoprost, brimonidine, timolol, sodium phosphate dibasic heptahydrate, citric acid monohydrate, sodium chloride, benzalkonium chloride, and sodium hydroxide in an aqueous carrier.

Embodiments disclosed herein also include methods of reducing IOP through the administration of compositions containing bimatoprost, brimonidine, and timolol. In another embodiment the brimonidine is a salt thereof, such as brimonidine tartrate, and the timolol is a salt thereof, such as timolol maleate. In yet another embodiment the administered compositions further contain sodium phosphate dibasic heptahydrate, citric acid monohydrate, sodium chloride, and sodium hydroxide in an aqueous carrier. In yet another embodiment the administered compositions further contain benzalkonium chloride.

In another embodiment the method of lowering IOP includes administering compositions containing 0.01% w/v bimatoprost, 0.15% w/v brimonidine tartrate, and 0.68% w/v timolol maleate. In yet another embodiment, the administered compositions further contain 1.5% w/v sodium phosphate dibasic heptahydrate, 0.025% w/v citric acid monohydrate, 0.35% w/v sodium chloride, sodium hydroxide, in an aqueous carrier. In yet another embodiment, the administered compositions further contain 0.005% w/v benzalkonium chloride.

Embodiments disclosed herein also include methods of reducing IOP through the administration of compositions described herein to subjects or patients. In certain embodiments the compositions described herein are administered to human subjects Embodiments disclosed herein also include methods of reducing IOP through the administration of compositions that consist essentially of bimatoprost, brimonidine, and timolol. In another embodiment the brimonidine is a salt thereof, such as brimonidine tartrate, and the timolol is a salt thereof, such as timolol maleate. In yet another embodiment the administered compositions further consist essentially of sodium phosphate dibasic heptahydrate, citric acid monohydrate, sodium chloride, and sodium hydroxide in an aqueous carrier. In yet another embodiment the administered compositions further consist essentially of benzalkonium chloride.

In another embodiment the method of lowering IOP includes administering compositions consisting essentially of 0.01% w/v bimatoprost, 0.15% w/v brimonidine tartrate, and 0.68% w/v timolol maleate. In yet another embodiment, the administered compositions further consist essentially of 1.5% w/v sodium phosphate dibasic heptahydrate, 0.025% w/v citric acid monohydrate, 0.35% w/v sodium chloride, and sodium hydroxide in an aqueous carrier. In yet another embodiment, the administered compositions further consist essentially of 0.005% w/v benzalkonium chloride.

Embodiments disclosed herein also include methods of reducing IOP through the administration of compositions that consist of bimatoprost, brimonidine, timolol, sodium phosphate dibasic heptahydrate, citric acid monohydrate, sodium chloride, and sodium hydroxide in an aqueous carrier. In another embodiment the brimonidine is the salt, brimonidine tartrate, and the timolol is the salt, timolol maleate. In yet another embodiment the administered compositions further consist of benzalkonium chloride.

In another embodiment the method of lowering IOP includes administering compositions consisting of 0.01% w/v bimatoprost, 0.15% w/v brimonidine tartrate, 0.68% w/v timolol maleate, 1.5% w/v sodium phosphate dibasic heptahydrate, 0.025% w/v citric acid monohydrate, 0.35% w/v sodium chloride, and sodium hydroxide in an aqueous carrier. In yet another embodiment, the administered compositions further consist of 0.005% w/v benzalkonium chloride.

Some embodiments of the present invention are included in the following paragraphs:

1) A pharmaceutical composition for lowering intraocular pressure in a patient suffering from elevated intraocular pressure comprising bimatoprost, brimonidine, and timolol.

2) The pharmaceutical composition of paragraph 1 wherein the pharmaceutical composition is effective in lowering intraocular pressure in patients who do not have adequate IOP control with mono or dual combination therapy.

3) The pharmaceutical composition of paragraph 1 wherein the brimonidine is brimonidine tartrate and the timolol is timolol maleate.

4) The pharmaceutical composition of paragraph 2 wherein the composition is applied topically and further comprising sodium phosphate dibasic heptahydrate, citric acid monohydrate, sodium chloride, and sodium hydroxide in an aqueous carrier.

5) The pharmaceutical composition of paragraph 3 further comprising benzalkonium chloride.

6) The pharmaceutical composition of paragraph 1 comprising about 0.01% w/v bimatoprost, about 0.15% w/v brimonidine tartrate and about 0.68% w/v timolol maleate.

7) The pharmaceutical composition of paragraph 5 further comprising about 0.005% w/v benzalkonium chloride.

8) A pharmaceutical composition for lowering IOP in patients suffering from elevated IOP who do not have adequate IOP control with mono or dual combination therapy consisting essentially of bimatoprost, brimonidine tartrate, timolol maleate, sodium phosphate dibasic heptahydrate, citric acid monohydrate, sodium chloride, and sodium hydroxide in an aqueous carrier.

9) The pharmaceutical composition of paragraph 8 further consisting essentially of benzalkonium chloride.

10) The pharmaceutical composition of paragraph 8 consisting essentially of about 0.01% w/v bimatoprost, about 0.15% w/v brimonidine tartrate, about 0.68% w/v timolol maleate, about 1.5% w/v sodium phosphate dibasic heptahydrate, about 0.025% w/v citric acid monohydrate and about 0.35% w/v sodium chloride.

11) The pharmaceutical composition of paragraph 10 consisting essentially of about 0.005% w/v benzalkonium chloride.

12) The pharmaceutical composition of paragraph 8 wherein said composition consists of bimatoprost, brimonidine tartrate, timolol maleate, sodium phosphate dibasic heptahydrate, citric acid monohydrate, sodium chloride, and sodium hydroxide in an aqueous carrier.

13) The pharmaceutical composition of paragraph 12 further consisting of benzalkonium chloride.

14) A method of reducing intraocular pressure (IOP) in a patient suffering from elevated IOP in patients who do not have adequate IOP control with mono or dual combination therapy comprising administering a topical pharmaceutical composition comprising bimatoprost, brimonidine, and timolol to the eye of a subject in need thereof.

15) The method of paragraph 14 wherein the pharmaceutical composition further comprises sodium phosphate dibasic heptahydrate, citric acid monohydrate, sodium chloride, and sodium hydroxide in an aqueous carrier.

16) The method of paragraph 15 wherein the pharmaceutical composition further comprises benzalkonium chloride and is applied to the eye at least once a day.

17) The method of paragraph 15 wherein said composition consists essentially of bimatoprost, brimonidine tartrate, timolol maleate, sodium phosphate dibasic heptahydrate, citric acid monohydrate, sodium chloride, and sodium hydroxide in an aqueous carrier.

18) The method of paragraph 16 wherein said composition is applied twice a day.

19) The method of paragraph 17 wherein said composition consists essentially of 0.01% w/v bimatoprost, 0.15% w/v brimonidine tartrate, 0.68% w/v timolol maleate, 1.5% w/v sodium phosphate dibasic heptahydrate, 0.025% w/v citric acid monohydrate and 0.35% w/v sodium chloride.

20) The method of paragraph 18 wherein said composition consists essentially of 0.005% w/v benzalkonium chloride.

DEFINITION OF TERMS

For the purposes of this disclosure, "treat," "treating," "treatment," or "therapy" refer to the use of a compound, composition, therapeutically active agent, or drug in the diagnosis, cure, mitigation, or treatment of the disease or underlying condition.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which can form in vivo as a result of administration of an acid, another salt, or a prodrug which is converted into an acid or salt.

Pharmaceutically acceptable salts of acidic functional groups can be derived from organic or inorganic bases. The salt can comprise a mono or polyvalent ion. Of particular interest are the inorganic ions lithium, sodium, potassium, calcium, and magnesium. Organic salts can be made with amines, particularly ammonium salts such as mono-, di- and trialkyl amines or ethanol amines. Salts can also be formed with caffeine, tromethamine and similar molecules. Hydrochloric acid or some other pharmaceutically acceptable acid can form a salt with a compound that includes a basic group, such as an amine or a pyridine ring.

A "prodrug" is a compound which is converted to a therapeutically active compound after administration, and the term should be interpreted as broadly herein as is generally understood by one of ordinary skill in the art. While not intending to limit the scope of this disclosure, conversion can occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester can be derived from a carboxylic acid of C1 (i.e. the terminal carboxylic acid of a natural prostaglandin), or an ester can be derived from a carboxylic acid functional group on another part of the molecule, such as on a phenyl ring. While not intending to be limiting, an ester can be an alkyl ester, an aryl ester, or a heteroaryl ester. The term alkyl has the meaning generally understood by those of ordinary skill in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, isobutyl, t-butyl, pentyl isomers, hexyl isomers, cyclopropyl, cyclobutyl, cyclopentyl, cyclohexyl, and combinations thereof having from 1-6 carbon atoms, etc.

DESCRIPTION

In a series of U.S. patent applications assigned to Allergan, Inc., prostaglandin esters with increased ocular hypotensive activity accompanied with substantially reduced side-effects are disclosed. U.S. patent application Ser. No. 386,835 (filed Jul. 27, 1989), relates to certain 11-acyl-prostaglandins, such as 11-pivaloyl, 11-acetyl, 11-isobutyryl, 11-valeryl, and 11-isovaleryl $PGF_{2\alpha}$ useful for lowering intraocular pressure (IOP). Intraocular pressure-reducing 15-acyl prostaglandins are disclosed in U.S. patent application Ser. No. 357,394 (filed May 25, 1989). Similarly, 11,15-9,15- and 9,11-diesters of prostaglandins, for example 11,15-dipivaloyl $PGF_{2\alpha}$ have ocular hypotensive activity. See U.S. patent application Ser. No. 385,645 (filed Jul. 27, 1990), now U.S. Pat. No. 4,994,274; U.S. patent application Ser. No. 584,370 (filed Sep. 18, 1990), now U.S. Pat. No. 5,028,624, which is a continuation of U.S. patent application Ser. No. 386,312 (filed Jul. 27, 1989), and U.S. patent application Ser. No. 585,284 (filed Sep. 18, 1990), now U.S. Pat. No. 5,034,413 which is a continuation of U.S. patent application Ser. No. 385,834 (filed Jul. 27, 1989). Each of these references is incorporated by reference herein in its entirety for its teachings regarding prostaglandin esters with ocular hypotensive activity.

Disclosed herein are compositions and methods for lowering IOP using a combination of at least three IOP-lowering agents, or pharmaceutical salts or prodrugs thereof including bimatoprost, brimonidine, and timolol. In certain embodiments, additional ingredients are added to the Triple Combination of bimatoprost, brimonidine, and timolol to make the composition more ophthalmically acceptable, including, without limitation, preservatives, buffers, tonicity adjusters, and surfactants. Additionally, various vehicles can be used in the disclosed embodiments. These compositions are useful in reducing IOP in patients with increased IOP, thus, for example, preventing or delaying glaucoma in those with ocular hypertension, and preventing or delaying further vision loss in those with glaucoma.

Without wishing to be bound by any particular theory, it is thought that the prostamide analog, bimatoprost (sold by Allergan, Inc. under the name LUMIGAN®) reduces IOP by increasing the aqueous humor outflow of an eye. Bimatoprost's chemical name is (Z)-7-[(1R,2R,3R,5S)-3,5-Dihydroxy-2-[1E,3S)-3-hydroxy-5-phenyl-1-pentenyl]cyclopentyl]-5-N-ethylheptenamide, and it has a molecular weight of 415.58.

Brimonidine, an α2-andrenergic agonist receptor, reduces the body's production of aqueous humor and increases the flow of aqueous humor out of the eye, resulting in a decrease in IOP. Brimonidine is available from Allergan, Inc. as ALPAHAGAN®. The chemical name of brimonidine tartrate, a salt of brimonidine, is 5-bromo-6-(2-imidazolidinylideneamino) quinoxaline L-tartrate. Brimonidine has a molecular weight of 442.24 as the tartrate salt.

Timolol, a non-selective β-adrenergic receptor blocking agent, reduces the body's aqueous humor production through the blockage of the β receptors on the ciliary epithelium. In one embodiment, the timolol component contains an acid salt of timolol and in another embodiment contains timolol maleate. The chemical name of timolol maleate, is (−)-1-tert-butylamino)-3-[(4-morpholino-1,2,5-thiodiazol-3yl) oxy]-2-propanol maleate (1:1) (salt). Timolol maleate has a molecular weight of 432.50. Timolol is commercially available from Merck as TIMOPTIC®.

Preservatives that can be used in the pharmaceutical compositions of the present embodiments include, but are not limited to, benzalkonium chloride, chlorobutanol, thimerosal, phenylmercuric acetate and phenylmercuric nitrate. Preservative-free compositions can be considered, in one non-limiting embodiment for patients experiencing hypersensitivity reactions with the above listed preservatives or other preservatives not listed.

Various buffers and means for adjusting pH can be used so long as the resulting preparation is ophthalmically acceptable. Accordingly, buffers include acetate buffers, citrate buffers, phosphate buffers and borate buffers. Acids or bases can also be used to adjust the pH of these formulations as needed. The pH of the disclosed compositions should preferably be maintained between 6.5 and 7.2 with an appropriate buffer system.

Tonicity adjustors can be added as needed and include, without limitation, glycerin, sorbitol, sodium chloride, potassium chloride, and mannitol, or any other suitable ophthalmically acceptable tonicity adjustor. In one embodiment the tonicity adjustor is sodium chloride.

In certain embodiments, a surfactant such as a polysorbate, for example, a TWEEN® by Sigma, can be added. Further, any other suitable surfactants can be used as well.

Various vehicles can also be used in the ophthalmic preparations of the present embodiments. These vehicles include, but are not limited to, polyvinyl alcohol, povidone, hydroxypropyl methyl cellulose, poloxamers, carboxymethyl cellulose, hydroxyethyl cellulose, physiological saline solution, water, purified water, and combinations thereof.

Additionally, ophthalmically acceptable antioxidants can be included in the disclosed compositions. Suitable antioxidants include, but are not limited to, sodium metabisulfite, sodium thiosulfate, acetylcysteine, butylated hydroxyanisole and butylated hydroxytoluene and the like and mixtures thereof.

Another excipient component that can be included in the ophthalmic preparations are chelating agents. A useful chelating agent is edetate disodium, although other chelating agents can also be used in place of or in conjunction edetate disodium.

Compositions and methods disclosed herein can also be used in combination with the following classes of drugs, pharmaceutically acceptable salts or prodrugs thereof:

β-Blockers (or β-adrenergic antagonists) including, without limitation, carteolol, levobunolol, metiparanolol, timolol hemihydrate, β1-selective antagonists such as betaxolol, and the like;

Adrenergic Agonists including, without limitation, non-selective adrenergic agonists such as epinephrine borate, epinephrine hydrochloride, and dipivefrin, and the like; and $α_2$-selective adrenergic agonists such as apraclonidine and the like;

Carbonic Anhydrase Inhibitors including, without limitation, acetazolamide, dichlorphenamide, methazolamide, brinzolamide, dorzolamide, and the like;

Cholinergic Agonists including, without limitation, direct acting cholinergic agonists such as carbachol, pilocarpine hydrochloride, pilocarbine nitrate, pilocarpine, and the like; Chlolinesterase inhibitors such as demecarium, echothiophate, physostigmine, and the like;

Glutamate Antagonists and other neuroprotective agents such as $Ca^{2+}$ channel blockers such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like;

Additional prostamides or pharmaceutically acceptable salts or prodrugs thereof;

Prostaglandins including travoprost, UFO-21, chloprostenol, fluprostenol, 13,14-dihydro-chloprostenol, isopropyl unoprostone, latanoprost and the like; and Cannabinoids including CB1 agonists such as WIN-55212-2 and CP-55940 and the like.

For treatment of diseases affecting the eye, the disclosed compositions can be administered topically or as ocular implants.

Pharmaceutical compositions can be prepared by combining a therapeutically effective amount of bimatoprost, brimonidine and timolol according to the present disclosure, or pharmaceutically acceptable acid addition salts thereof, as active ingredients, with conventional ophthalmically acceptable pharmaceutical excipients, and by preparation of unit dosage forms suitable for ocular use. The therapeutically efficient amount will vary with the activity of the active ingredients; however, typically in combination will be between 0.0001 and 20% (w/v), between 0.0001 and 10% (w/v), between 0.0001 and 5% (w/v), between 0.0005 and 3% (w/v), between 0.00075 and 2% (w/v), between 0.001 and 1.0% (w/v), between 0.2 and 1.0% (w/v), between 0.5 and 1.0% (w/v), 0.85% (w/v) or 0.843% (w/v) of the composition. The compositions can be prepared as follows:

1. Add quantity of water i.e. approximately 70% of the batch size in a chosen stainless steel vessel.
2. Add Sodium Phosphate Dibasic Heptahydrate to step 1 under mechanical stirring and mix until dissolved.
3. Add Citric Acid Monohydrate to step 2 under stirring and mix until dissolved.
4. Add Sodium Chloride to step 3 under stirring and mix until dissolved.
5. Add bimatoprost to step 4 under stirring and mix until a clear solution is obtained.
6. Add timolol maleate to step 5 under stirring and mix until dissolved.
7. Add brimonidine tartrate to step 6 under stirring and mix until dissolved.
8. Add benzalkonium chloride to step 7 as a stock solution under stirring.
9. Check pH of the solution, adjust if necessary to pH 7.1
10. Make up the volume to 100% of the batch size with water and stir for 5-10 minutes.

Bimatoprost can be included in compositions of the embodiments disclosed herein in an amount of between 0.0001 and 15% (w/v), between 0.0001 and 10% (w/v), between 0.0001 and 5% (w/v), between 0.0005 and 3% (w/v), between 0.00075 and 2% (w/v), between 0.001 and 1.0% (w/v), between 0.001 and 0.1 (w/v), between 0.005 and 0.05% (w/v), or 0.01% (w/v) of the composition.

Brimonidine can be included in compositions of the embodiments disclosed herein in an amount of between 0.0001 and 15% (w/v), between 0.0001 and 10% (w/v), between 0.0001 and 5% (w/v), between 0.0005 and 3% (w/v), between 0.00075 and 2% (w/v), between 0.001 and 1.0% (w/v), between 0.001 and 0.2 (w/v), between 0.005 and 0.05% (w/v), or 0.15% (w/v) of the composition. In one embodiment brimonidine is provided as brimonidine tartrate in an amount of 0.15% (w/v) of the composition.

Timolol can be included in compositions of the embodiments disclosed herein in an amount of between 0.0001 and 15% (w/v), between 0.0001 and 10% (w/v), between 0.0001 and 5% (w/v), between 0.0005 and 3% (w/v), between 0.01 and 2% (w/v), between 0.1 and 1.0% (w/v), between 0.1 and 0.9 (w/v), between 0.3 and 0.8% (w/v), 0.5%, 0.6% (w/v), 0.68% (w/v/) or 0.683% (w/v) of the composition. In one embodiment timolol is provided as timolol maleate in an amount of 0.6%, 0.68% or 0.683% (w/v) of the composition.

The amount of the presently useful compositions administered is dependent on the therapeutic effect or effects desired, on the specific patient being treated, on the severity and nature of the patient's condition, on the manner of administration, on the potency and pharmacodynamics of the particular compound or compounds employed, and on the judgment of the prescribing physician. The therapeutically effective dosage of the presently useful compositions can be in the range of 0.01 to 200 mg/kg/day. In certain embodiments, the therapeutically effective dosage can be 0.1, 0.5, 1, 2.5, 5, 15, 20, 25, 50, 60, 70, 75, 80, 85, 90 or 100 mg/kg/day. The dosage can be provided in a single daily dosage or in a number of doses from 2 to 24 over the course of day. In certain embodiments, dosages can be administered every other day, every third day, once a week, once a month, etc. . . .

In preferred embodiments, the comfort of formulations disclosed herein is maximized as much as possible, although sometimes formulation considerations (e.g. drug stability) can necessitate less than optimal comfort. In the case that comfort cannot be maximized, the compositions should be formulated such that the compositions are tolerable to the patient for ophthalmic use.

The ophthalmic formulations of the present disclosure are conveniently packaged in forms suitable for metered application, such as in containers equipped with a dropper, to facilitate application to the eye. Containers suitable for dropwise application are usually made of suitable inert, non-toxic plastic material, and generally contain between 0.5 and 15 ml solution. One package can contain one or more unit doses.

Preservative-free solutions (e.g., Table 7) can be formulated in non-resealable containers containing up to 1, 2, 5, 10, 50, or 100 unit doses, where a typical unit dose is from 1 to 8 drops. The volume of one drop generally will be from 20 to 35 µl.

Various exemplary embodiments can be formulated as shown in the Tables follows:

TABLE 1

| Ingredients | Amount (% w/v) |
|---|---|
| Active Ingredients | 0.001-5 |
| Preservative | 0-0.10 |
| Vehicle | 0-40 |
| Tonicity Adjuster | 1-10 |
| Buffer | 0.01-10 |
| pH Adjuster | q.s. pH 4.5-7.5 |
| Antioxidant | As needed |
| Surfactant | As needed |
| Purified Water | As needed to make 100% |

TABLE 2

| Ingredient | Function | % w/v |
|---|---|---|
| Bimatoprost | Active | 0.003-0.03 |
| Brimonidine | Active | 0.005-0.2 |
| Timolol | Active | 0.2-0.5 |
| Sodium Phosphate Dibasic Heptahydrate | Buffering Agent | As needed to make ophthalmically acceptable |
| Citric Acid Monohydrate | Buffering Agent | As needed to make ophthalmically acceptable |
| Sodium Chloride | Tonicity Agent | As needed to make ophthalmically acceptable |
| Sodium Hydroxide | pH Adjuster | q. s. |
| Water | Vehicle | q. s. |

TABLE 3

| Ingredient | Function | % w/v |
|---|---|---|
| Bimatoprost | Active | 0.003-0.03 |
| Brimonidine Tartrate | Active | 0.005-0.3 |
| Timolol Maleate | Active | 0.2-0.8 |
| Sodium Phosphate Dibasic Heptahydrate | Buffering Agent | 1.0-2.0 |
| Citric Acid Monohydrate | Buffering Agent | 0.01-0.05 |
| Sodium Chloride | Tonicity Agent | 0.10-0.30 |

TABLE 3-continued

| Ingredient | Function | % w/v |
|---|---|---|
| Sodium Hydroxide | pH Adjuster | q.s. |
| Water | Vehicle | q.s. |

TABLE 4

| Ingredient | Function | % w/v |
|---|---|---|
| Bimatoprost | Active | 0.003-0.03 |
| Brimonidine | Active | 0.005-0.2 |
| Timolol | Active | 0.2-0.5 |
| Sodium Phosphate Dibasic Heptahydrate | Buffering Agent | As needed to make ophthalmically acceptable |
| Citric Acid Monohydrate | Buffering Agent | As needed to make ophthalmically acceptable |
| Sodium Chloride | Tonicity Agent | As needed to make ophthalmically acceptable |
| Benzalkonium Chloride | Preservative | As needed to make ophthalmically acceptable |
| Sodium Hydroxide | pH Adjuster | q.s. |
| Water | Vehicle | q.s. |

TABLE 5

| Ingredient | Function | % w/v |
|---|---|---|
| Bimatoprost | Active | 0.01 |
| Brimonidine Tartrate | Active | 0.1 |
| Timolol Maleate | Active | 0.6 |
| Sodium Phosphate Dibasic Heptahydrate | Buffering Agent | 1.5 |
| Citric Acid Monohydrate | Buffering Agent | 0.025 |
| Sodium Chloride | Tonicity Agent | 0.35 |
| Sodium Hydroxide | pH Adjuster | q.s. |
| Water | Vehicle | q.s. |

TABLE 6

| Ingredient | Function | % w/v |
|---|---|---|
| Bimatoprost | Active | 0.01 |
| Brimonidine Tartrate | Active | 0.1 |
| Timolol Maleate | Active | 0.6 |
| Sodium Phosphate Dibasic Heptahydrate | Buffering Agent | 1.5 |
| Citric Acid Monohydrate | Buffering Agent | 0.025 |
| Sodium Chloride | Tonicity Agent | 0.35 |
| Benzalkonium Chloride | Preservative | 0.005 |
| Sodium Hydroxide | pH Adjuster | q.s. |
| Water | Vehicle | q.s. |

TABLE 7

| Ingredient | Function | % w/v |
|---|---|---|
| Bimatoprost | Active | 0.01 |
| Brimonidine Tartrate | Active | 0.15 |
| Timolol Maleate | Active | 0.68 |
| Sodium Phosphate Dibasic Heptahydrate | Buffering Agent | 1.5 |
| Citric Acid Monohydrate | Buffering Agent | 0.025 |
| Sodium Chloride | Tonicity Agent | 0.35 |
| Sodium Hydroxide | pH Adjuster | q.s. |
| Water | Vehicle | q.s. |

TABLE 8

| Ingredient | Function | % w/v |
|---|---|---|
| Bimatoprost | Active | 0.01 |
| Brimonidine Tartrate | Active | 0.15 |
| Timolol Maleate | Active | 0.68 |
| Sodium Phosphate Dibasic Heptahydrate | Buffering Agent | 1.5 |
| Citric Acid Monohydrate | Buffering Agent | 0.025 |
| Sodium Chloride | Tonicity Agent | 0.35 |
| Benzalkonium Chloride | Preservative | 0.005 |
| Sodium Hydroxide | pH Adjuster | q.s. |
| Water | Vehicle | q.s. |

TABLE 9

| Ingredient | Function | % w/v |
|---|---|---|
| Bimatoprost | Active | 0.01 |
| Brimonidine Tartrate | Active | 0.15 |
| Timolol Maleate | Active | 0.683 (equivalent to 0.5 timolol) |
| Sodium Phosphate Dibasic Heptahydrate | Buffering Agent | 1.5 |
| Citric Acid Monohydrate | Buffering Agent | 0.025 |
| Sodium Chloride | Tonicity Agent | 0.35 |
| Sodium Hydroxide | pH Adjuster | q.s. |
| Water | Vehicle | q.s. |

TABLE 10

| Ingredient | Function | % w/v |
|---|---|---|
| Bimatoprost | Active | About 0.01 |
| Brimonidine Tartrate | Active | About 0.15 |
| Timolol Maleate | Active | About 0.683 |
| Sodium Phosphate Dibasic Heptahydrate | Buffering Agent | About 1.5 |
| Citric Acid Monohydrate | Buffering Agent | About 0.025 |
| Sodium Chloride | Tonicity Agent | About 0.35 |
| Benzalkonium Chloride | Preservative | About 0.005 |
| Sodium Hydroxide | pH Adjuster | q.s. |
| Water | Vehicle | q.s. |

*"About" refers to variations in the concentrations which would be considered bioequivalent by a regulatory agency Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Example I—Triple Combination of Bimatoprost, Brimonidine and Timolol

Thirty-six female New Zealand White rabbits, obtained from Charles River Laboratories, Wilmington, Mass., 4 months old, and weighing from 2.96 to 3.54 kilograms at the start of dosing, were used for the study. One drop (~30 μL/drop) of the formulation of Table 11 was administered directly onto the superior corneal surface of the left eye using a dropper bottle 2 or 4 times daily (2 or 6 hour intervals) for 1 month.

TABLE 11

| Ingredient | Function | % w/v |
|---|---|---|
| Bimatoprost | Active | 0.01 |
| Brimonidine Tartrate | Active | 0.15 |
| Timolol Maleate | Active | 0.683* |
| Sodium Phosphate Dibasic Heptahydrate | Buffering Agent | 1.5 |
| Citric Acid Monohydrate | Buffering Agent | 0.025 |
| Sodium Chloride | Tonicity Agent | 0.35 |
| Benzalkonium Chloride | Preservative | 0.005 |
| Sodium Hydroxide | pH adjuster | q.s. |
| Water | Vehicle | q.s. |

*Equivalent to 0.5% w/v timolol

The contralateral right eye served as an untreated control. Dose administration and time of dosing are manually recorded onto raw data sheets, and the worksheets serve as the official record of dosing.

The intraocular pressure (IOP) in both eyes of all rabbits was measured prior to initiation of dosing and at the end of the 1-month interim period. Future examinations will occur at the end of the 3-month treatment period and following the 1-month recovery period. IOP measurements are performed at approximately the same time each examination day. An ophthalmic topical anesthetic (eg, proparacaine HCl), is administered to the eye prior to measurements. If deemed necessary, the eye is rinsed with sterile saline at the completion of the measurement. IOP measurements are manually recorded on raw data sheets.

In conclusion, female NZW rabbits (12/group) were administered one topical ocular drop (~30 μL/drop) of Triple Combination or Triple Combination Placebo two or four times daily in the left eye for 1 month. No drug-related effects were observed in ophthalmology, gross ocular observations, body weight, clinical observations, or food consumption. Expected, acceptable drug-related decreases in intraocular pressure were observed in rabbits given Triple Combination Ophthalmic Solution. Triple Combination Ophthalmic Solution was well-tolerated.

TABLE 12

OS—Triple Combination Ophthalmic Solution, 50 ppm
BAK, (1 drop~30 μL, 4 X/day)
OD—Untreated

| Study Animal | OS | | OD | |
|---|---|---|---|---|
| Number | Baseline | Day 27 | Baseline | Day 27 |
| 350 | 9 | 9 | 9 | 9 |
| 351 | 13 | 8 | 12 | 8 |
| 352 | 11 | 8 | 11 | 9 |
| 353 | 9 | 8 | 9 | 10 |
| 354 | 10 | 8 | 11 | 9 |
| 355 | 12 | 9 | 11 | 9 |
| 356 | 11 | 9 | 13 | 9 |
| 357 | 10 | 7 | 11 | 8 |
| 358 | 12 | 9 | 11 | 9 |
| 359 | 11 | 9 | 10 | 10 |
| 360 | 10 | 9 | 11 | 10 |
| 361 | 12 | 9 | 12 | 10 |
| Mean (n = 12) | 10.8 | 8.5 | 10.9 | 9.2 |
| SD | 1.3 | 0.7 | 1.2 | 0.7 |
| % Change from Baseline | — | −21.5 | — | −16.0 |
| % Change from OD | −0.8 | −7.3 | — | — |
| % Change from Placebo | 0.8 | −19.0 | −5.8 | −19.1 |

OS = Left eye;
OD = Right eye;
Baseline = Day −6;
"—" = Not applicable
% change from baseline = [(mean − baseline mean) ÷ baseline mean] × 100
% change from OD = [( mean OS − mean OD) ÷ mean OD] × 100.

Example II—IOP Lowering Effect of the Triple Combination Product of Table 11

A 71 year old Caucasian male is suffering from open angle glaucoma and elevated intraocular pressure which is threatening to worsen his vision if left untreated. After three months on combination therapy, the patient's IOP was not lowered to the satisfaction of his physician. The 71 year old Caucasian begins daily dosing in both eyes of the Triple Combination of Table 11 and the patient is expected to experience adequate lowering of IOP that was not achievable.

Example III—IOP Lowering of the Triple Combination Product of Table 11 in a 64 Year African American Female A 64 year old African American female suffering from glaucoma is having difficulty lowering her IOP adequately with combination therapy product of brimonidine and timolol. After four months of combination therapy of the brimonidine and timolol product, her physician switches her to the Triple Combination therapy product in Table 11. After three weeks on the Triple Combination therapy product, the patient's IOP in both eyes is expected to be at acceptable levels.

Example III—Treatment of Glaucoma of a 57 Year Old Caucasian Female

A 57 year old Caucasian female suffering from open-angle glaucoma has been largely non-responsive to first monotherapy and then combination therapy for lowering IOP. She switches to twice daily dosing of the composition in Table 11 and her IOP is expected to return to normal levels. After 30 days of dosing both eyes with the formulation of Table 11, the 57 year old Caucasian female's IOP returns to normal levels as long as she continues dosing with the formulation of Table 11.

Example IV—Treatment of Elevated Intraocular Pressure in a 61 Year Old Asian Male A 61 year old Asian male IOP was measured with a tonometer as being between 21.3 mmHg and 23.7 mmHg. Both monotherapy and combination therapy with various therapeutic agents known to lower IOP failed to bring the patient's IOP to acceptable levels. The patient began taking twice a day administration of the formulation of Table 11, with a single drop per eye in the morning and a single drop per eye 12 hours later in the evening. After 31 days, the patient's IOP is expected to lower to between 16.1-18.2 mmHg which is considered acceptable. After 90 days, the patient's IOP is expected to lower to between 15.5-16.8 mmHg.

Example V—A Multicenter, Open-Label Study to Evaluate the Safety and Efficacy of Twice-Daily 0.01% Bimatoprost/0.15% Brimonidine/0.5% Timolol Ophthalmic Solution (Triple Combination) in Patients in India, in Who have Glaucoma or Ocular Hypertension with Elevated IOP, and are on Twice-Daily 0.2% Brimonidine/0.5% Timolol Ophthalmic Solution (Dual Combination) Therapy Phase: 3
Name of Investigational Product: 0.01% Bimatoprost/0.15% Brimonidine/0.5% Timolol Ophthalmic Solution
Brief Description: Multicenter, Open-label, Phase 3 Study
Objectives: To evaluate the efficacy, safety and tolerability of twice-daily dosed Triple Combination ophthalmic solution administered for 12 weeks in patients, who have glaucoma or ocular hypertension with elevated intraocular pressure (IOP), and were on twice-daily 0.2% brimonidine/0.5% timolol ophthalmic solution (either as COMBIGAN or as individual monotherapies, hereafter referred to as Dual Combination) therapy.
Methodology:
This was a 12-week, multicenter, open label study of Triple Combination. Patients administered study medications twice-daily in each eye for 12 weeks. Prior to study entry, patients received Dual Combination for at least 1 month. At baseline, patients transitioned to open-label Triple Combination and were followed post-baseline for 12 weeks. There were 5 scheduled visits (prestudy, baseline [day 0], week 4, week 8, and week 12).

Triple Combination is a fixed combination ophthalmic solution containing bimatoprost 0.01%, timolol 0.5%, and brimonidine 0.15%. Each of these active drug substances is available as individual monotherapies or as fixed-combinations of 2 of the 3 components. The inactive ingredients are: BAK (50 ppm) as preservative, sodium chloride, sodium phosphate dibasic, citric acid, and purified water.

Triple Combination ophthalmic solution was instilled twice daily, at approximately 12 hour intervals for 12 weeks. As the individual components have different dosing frequencies (bimatoprost is dosed once daily, timolol once or twice daily, and brimonidine is dosed twice daily), Triple Combination is dosed twice daily. The concentrations of the active drug substances in Triple Combination are at or less than when given concurrently, and expose a patient too less BAK per dose. The overall daily exposure to BAK with Triple Combination is less than that of the concurrent use of the individual components. Bimatoprost 0.01% once daily, timolol twice daily and ALPHAGAN P twice daily exposes a patient to 400 ppm BAK daily (LUMIGAN 0.01% has 200 ppm BAK, timolol 0.5% has 100 ppm BAK, and brimonidine 0.15% [ALPHAGAN P] has 0 ppm BAK), whereas Triple Combination exposes a patient to 100 ppm daily [50 ppm per dose]).

This was a multicenter, open-label study to evaluate the safety, tolerability, and efficacy of Triple Combination ophthalmic solution administered twice daily in each eye for 12 weeks in Indian patients with glaucoma or ocular hypertension with elevated IOP on Dual Combination. This study represents the first administration of this Triple Combination ophthalmic solution to human subjects.

Triple Combination was prescribed to patients who did not have adequate IOP control with dual combination. Thus, patients with glaucoma or ocular hypertension while on Dual Combination (brimonidine plus timolol) during the run-in period were an appropriate population in which to assess the effects of Triple Combination.

The primary efficacy measure, IOP, was assessed using the "gold standard" instrument to measure IOP, the Goldmann applanation tonometer (GAT). The primary efficacy variable was change from baseline in the study eye mean diurnal IOP at week 12, an accepted variable for studies evaluating IOP. Safety assessments were adverse events (ocular and non-ocular), pulse rate, blood pressure, visual acuity, biomicroscopy, ophthalmoscopy, cup/disc ratio, visual fields (VFs), and pregnancy tests (for females of childbearing potential).
Number of Patients (Planned and Enrolled):
Planned: A total of 120 patients were planned to be enrolled.
Enrolled: A total of 126 patients were enrolled in the study.
Diagnosis and Main Criteria for Eligibility:
Male or female patients 18 years of age or older, with a diagnosis of glaucoma or ocular hypertension in each eye and who had elevated IOP requiring bilateral administration of IOP-lowering treatment.
Test Product, Dose and Mode of Administration:
0.01% bimatoprost/0.15% brimonidine/0.5% timolol ophthalmic solution.
Duration of Treatment: 12 weeks.
Safety Measures:
The safety measures in this study included: adverse events, pulse rate, blood pressure, visual acuity, biomicroscopy, ophthalmoscopy and cup/disc ratio, visual field examinations, and pregnancy testing for females of childbearing potential.
Adverse Events:
An adverse event was defined as any untoward medical occurrence in a patient or clinical investigation patient administered a pharmaceutical product and that does not necessarily have a causal relationship with this treatment. An adverse event could therefore be any unfavorable and unintended sign (including an abnormal laboratory finding), symptom, or disease temporally associated with the use of a medicinal (investigational) product, whether or not related to the medicinal (investigational) product.
Adverse events were monitored throughout the study.
Serious Adverse Events:
A serious adverse event was defined as any adverse event occurring at any dose that resulted in any of the following outcomes: death, a life-threatening adverse event, inpatient hospitalization or prolongation of existing hospitalization, a persistent or significant disability/incapacity, or a congenital anomaly/birth defect. Important medical events that may not result in death, be life-threatening, or require hospitalization could have been considered a serious adverse event when, based upon appropriate medical judgment, they could have jeopardized the patient or subject and could have required medical or surgical intervention to prevent one of the outcomes listed in this definition.
Serious Medical Event:
A serious medical event was defined as a medical event satisfying the same criteria as a serious adverse event, but the event occurred between the obtaining of informed consent and entry into the study.

Severity:

A clinical determination of the intensity of an adverse event, serious adverse event, or serious medical event was completed using the following definitions as guidelines:

Mild: Awareness of sign or symptom, but easily tolerated;
Moderate: Discomfort enough to cause interference with usual activity;
Severe: Incapacitating with inability to work or do usual activity; and,
Not applicable: In some cases, an adverse event could be an 'all or nothing' finding which could not be graded.

Relationship to Study Drug:

A determination was made regarding the relationship (if any) between an adverse event and the study drug. A causal relationship was present if a determination was made that there was a reasonable possibility that the adverse event may have been caused by the drug.

Pulse Rate:

Pulse rate was recorded as beats per minute and measured with patients in a resting state (seated) for at least 5 minutes.

Systolic and Diastolic Blood Pressure:

Systolic and diastolic blood pressures were measured by sphygmomanometer with patients in a resting state (seated upright) for at least 5 minutes and recorded in mm Hg, using the same arm each time.

Visual Acuity:

Best corrected visual acuity was measured for each eye using a logarithmic visual acuity chart for testing at 10 feet (approximately 3 meters). Snellen equivalent units were entered on the appropriate CRF (eg, 20/20).

Biomicroscopy:

Biomicroscopy was performed without pupil dilation using slit lamp examination. The examinations included evaluation of the conditions of the lids, lid margins, conjunctiva, anterior chamber, and cornea.

Ophthalmoscopy and Cup/Disc Ratio:

Lens, vitreous, and fundus pathology observations were made through a dilated pupil. In addition, cup/disc ratio was measured using direct and indirect ophthalmoscopy, and the Allergan Armaly chart. Evaluations were performed after the IOP examination of the relevant visits.

Visual Field Examinations:

Visual field examinations (including historical tests for the prestudy visit) were performed using either Humphrey or Octopus automated perimetry. Acceptable test methods were Humphrey 24-2 (full threshold or Swedish Interactive Thresholding Algorithm Standard) and Octopus G1 or 24-2 programs and Dynamic or Normal strategies. Visual fields were reported as normal or abnormal and the mean deviation/mean defect/mean loss was also recorded in decibels.

Efficacy and Safety Measures:

Efficacy: IOP as measured by Goldmann applanation tonometry.

Safety: Adverse events, pulse rate, systolic and diastolic blood pressure, visual acuity, biomicroscopy, ophthalmoscopy and cup/disc ratio, visual field examinations, and pregnancy testing.

Statistical Methods:

There were three analysis populations: a safety population, a modified intent-to-treat (mITT) population, and a per-protocol (PP) population. One study site was identified as having major Good Clinical Practice (GCP) violations. The data for this site were not included in any of the three analysis populations. Sensitivity analyses were performed for efficacy and safety to confirm that the removal of this site did not impact the results. With the exception of the patients from this site, the safety population included all treated patients; the mITT population included all enrolled patients with a baseline and at least one postbaseline efficacy evaluation; the PP population included all patients who had no major protocol violations, received study medication, and had at-least one follow-up visit. The mITT and PP populations were used for the efficacy analyses and the safety population was used for all safety analyses.

In general, continuous variables were summarized by descriptive statistics including sample size, mean, standard deviation (SD), median, and minimum and maximum. Categorical variables were summarized by frequency and percentage.

The primary efficacy variable was change from baseline (on Dual Combination) in the study eye mean diurnal IOP at week 12 (on Triple Combination) in the mITT population. The null hypothesis was that there was no difference between the week 12 and baseline visits in study eye mean diurnal IOP. The alternative hypothesis was that Triple Combination will decrease (from baseline) study eye mean diurnal IOP at week 12. This hypothesis was tested using a 2-sided 1-sample t-test. Adverse events were coded using the Medical Dictionary for Regulatory Activities nomenclature. The preferred terms were summarized by primary system organ class and maximum severity for all events (regardless of causality), treatment-related adverse events, serious adverse events, and adverse events that lead to study withdrawal.

Data Conventions:

The following data conventions were applied to all analyses.

For efficacy analyses in the mITT population, unless otherwise specified or implied, the missing values were imputed using the method of last-observation-carried-forward (LOCF) from the most recent preceding scheduled visit with nonmissing data and corresponding hour. For example, if hour 8, week 12 IOP was missing, the value at hour 8, week 8 (if nonmissing) was used for imputation. If necessary, baseline values were carried forward.

Descriptive statistics (number of observations (n), arithmetic mean (mean), SD, median, minimum and maximum [range]) were presented in the summary tables for continuous data. For categorical data, frequency counts (n) and percentages (%) were presented. The percentages were based on the population under consideration.

Patient-wise data listings were generated. The listings were sorted by site number followed by the patient number. The age, sex, and race of patients were included in each listing.

Day 0 was the baseline visit. No data imputation for missing baseline values was performed.

Days from baseline (day 0) were calculated as:

Treatment days=visit date−day 0 visit date+1

Study days=visit date−day 0 visit date

The change from baseline value was computed as the value for a given visit minus the baseline value, unless otherwise indicated.

Partial dates were treated as missing in computations, but were listed in the data listings as they appeared on the CRFs unless otherwise specified. No imputation of missing values was performed unless otherwise specified.

Primary Efficacy Analysis:

The primary efficacy variable was derived from the IOP measurements. Each IOP assessment consisted of 2 consecutive measurements in each eye. If these 2 measurements differed by >2 mm Hg, a third measurement was performed.

If 2 measurements were obtained, the IOP value for a given eye was the average of the 2 measurements. If the first 2 measurements differed by >2 mm Hg, the IOP value for the given eye was the median of the 3 measurements. The study eye was defined as the eye that met the enrollment criteria. If both eyes met the enrollment criteria, then the eye with the higher IOP was considered the study eye. If both eyes met all criteria and had the same IOP, then the right eye was deemed the study eye.

The primary efficacy variable was the change from baseline (day 0) in study eye mean diurnal IOP at the week 12 visit in the mITT population. The mean diurnal IOP is calculated as the mean of the IOP values (mean of hour 0, hour 2 and hour 8 IOPs) at each visit. The null hypothesis was that there was no difference between the week 12 and baseline visits in study eye mean diurnal IOP. The alternative hypothesis was that Triple Combination would decrease (from baseline) study eye mean diurnal IOP at week 12.

Descriptive statistics were provided for baseline and change from baseline in mean diurnal IOP at week 12. The null hypothesis was tested using a 1-sample t-test. A point estimate of the mean change from baseline and the corresponding 95% confidence interval was provided. The null hypothesis was rejected and Triple Combination was considered superior to Dual Combination if the two-sided p-value was ≤0.05 and the point estimate of the mean change from baseline was negative.

Other Efficacy Analysis:

Analysis on the change from baseline in mean diurnal IOP was performed for all scheduled postbaseline visits through week 12, in the study eye using the mITT and PP populations.

Safety Analysis:

All the safety analyses were performed on patients in the safety population.

For all safety data collected from ophthalmic examination, the analysis for each visit was based on the examination of the eye with the worst outcome as compared with the baseline.

No imputation for missing data was performed for the safety population.

Adverse events were listed. The number and percent of patients experiencing an event were tabulated for each system organ class (SOC) and preferred term (PT). Adverse events were also tabulated according to severity and causality. All aforementioned analyses were performed for ocular adverse events separately. Ocular adverse events are determined based on the investigator indicating that the adverse event was related to the eye on the adverse event data collection form and thus were not limited to adverse events in the 'eye disorders' SOC. Serious adverse events were listed separately.

Individual data listings of vital signs (observed and change from baseline) were presented for each patient. Individual clinically significant vital sign findings that were considered adverse events by the investigator were presented in the adverse event listings. Observed values as well as change from baseline data were summarized descriptively in tabular format by treatment group.

Other Safety Analysis:

The BCVA (change from baseline in the number of lines read at the final visit) was calculated for each eye. The data was tabulated by the number and percentage of patients for the eye with the worse line change.

The number and percent of patients experiencing clinically significant biomicroscopy/ophthalmoscopy findings were tabulated by PT. Clinically significant biomicroscopy/ophthalmoscopy findings were also tabulated according to mean severity grade and the frequency distribution of severity scores.

Cup/disc ratio (change from baseline) was calculated and tabulated data was presented by the number and percentage of patients for the eye with the worse change.

Determination of Sample Size:

Sample size was calculated based on the primary efficacy variable and combined data from GANFORT pivotal studies in which the SD for change from baseline (based on the study eye defined in this protocol) in mean diurnal IOP at month 3 was 3.22 mm Hg for GANFORT-treated patients. It was expected that with Triple Combination the IOP-lowering effect would be at least 1 mm Hg greater than with the Dual Combination (ie, the change from baseline in mean diurnal IOP would be at least 1 mm Hg). With a sample size of 112, a single group t-test with a 0.025 1-sided significance level had 90% power to detect a mean decrease in IOP of 1.0 mm Hg between Dual and Triple Combination, assuming that the SD was 3.22. In the GANFORT pivotal studies, the discontinuation rate was approximately 7% at month 3. Allowing for a similar discontinuation rate, 120 patients were planned to be enrolled into this study to provide approximately 112 completed patients.

Primary Efficacy: Change from Baseline in Mean Diurnal IOP at Week 12 in the Modified Intent-to-treat Population:

At week 12, the mean change from baseline in study eye mean diurnal IOP was −3.98 mm Hg (p<0.001) demonstrating that Triple Combination provided a clinically meaningful and statistically significant additional IOP reduction from the Dual Combination-treated baseline. A summary of study eye mean diurnal IOP and change from baseline in mean diurnal IOP by visit for the mITT population is provided in Table 13.

TABLE 13

Summary of Study Eye Mean Diurnal IOP by Visit (Modified Intent-to-treat Population)

| Visit | Statistics | TRIPLE COMBINATION GROUP (N = 121) |
|---|---|---|
| Baseline | N | 121 |
| | Mean (SD) | 22.35 (3.417) |
| | Median; Range (Min, Max) | 21.50; (16.5, 35.7) |
| Week 4 | N | 121 |
| | Mean (SD) | 17.87 (3.621) |
| | Median; Range (Min, Max) | 17.33; (11.0, 33.3) |
| Change from Baseline to Week 4 | N | 121 |
| | Mean (SD) | −4.49 (3.018) |
| | Median; Range (Min, Max) | −4.00; (−13.0, 3.0) |
| | 95% CI [a] | (−5.0, −3.9) |
| | p-value [a] | <0.001 |
| Week 8 | N | 121 |
| | Mean (SD) | 18.13 (3.669) |
| | Median; Range (Min, Max) | 17.83; (11.2, 34.0) |
| Change from Baseline to Week 8 | N | 121 |
| | Mean (SD) | −4.22 (2.795) |
| | Median; Range (Min, Max) | −4.20; (−15.0, 1.8) |
| | 95% CI [a] | (−4.7, −3.7) |
| | p-value [a] | <0.001 |
| Week 12 | N | 121 |
| | Mean (SD) | 18.37 (3.732) |
| | Median; Range (Min, Max) | 18.00; (10.7, 34.0) |
| Change from Baseline to Week 12 | N | 121 |
| | Mean (SD) | −3.98 (2.856) |
| | Median | −4.00 |
| | Range (Min, Max) | −12.7, 3.0 |

TABLE 13-continued

Summary of Study Eye Mean Diurnal IOP by Visit
(Modified Intent-to-treat Population)

| Visit | Statistics | TRIPLE COMBINATION GROUP (N = 121) |
|---|---|---|
| | 95% CI [a] | (−4.5, −3.5) |
| | p-value [a] | <0.001 |

Min = minimum;
max = maximum;
SD = standard deviation
Note:
Study eye is the eye that met the IOP inclusion criteria at baseline hour 0 (>18 and <34 mm Hg); it is the eye with the higher IOP values if both eyes met the criteria; it is the right eye if both eyes had the same IOP values or neither eye met the inclusion criteria. The mean diurnal IOP at each visit is the mean IOP of hour 0, hour 2, and hour 8. Missing value at each visit is imputed by Last Observation Carried Forward before mean diurnal at the visit is calculated.
[a] confidence interval (CI) and p-value are obtained by using 1 sample t-test.

Other Efficacy:

The other efficacy analyses included change from baseline (day 0) in study eye mean diurnal IOP at the week 12 visit using the PP population and at weeks 4, and 8 using the mITT and PP populations.

In the mITT population, at weeks 4 and 8, the mean change from baseline in study eye mean diurnal IOP were −4.49 and −4.22, respectively (p<0.001) demonstrating that Triple Combination provided a clinically meaningful and statistically significant additional IOP reduction from the Dual Combination-treated baseline at both visits.

In the PP population, at weeks 4, 8, and 12, the mean changes from baseline in study eye mean diurnal IOP were −4.64, −4.14, and −4.22, respectively. The changes were clinically and statistically significant and similar to those of the mITT population.

Sub-Group Analysis of Efficacy Variables:

Results similar to those seen in the overall mITT population were also observed for each age subgroup (≤65 years and >65 years) for the primary efficacy variable, demonstrating that Triple Combination provided a clinically meaningful and statistically significant additional IOP reduction from the Dual Combination-treated baseline in both subgroups.

In the subgroup of patients that were ≤65 years of age in the mITT population, at weeks 4, 8, and 12, the mean changes from baseline in study eye mean diurnal IOP were −4.67, −4.41, and −4.04, respectively (p<0.001).

In the subgroup of patients that were >65 years of age in the mITT population, at weeks 4, 8, and 12, the mean change from baseline in study eye mean diurnal IOP were −3.94, −3.66, and −3.80, respectively (p<0.001).

Efficacy Conclusions:

At week 12, Triple Combination provided a clinically meaningful and statistically significant additional IOP-lowering effect from the Dual Combination-treated baseline. The mean changes from baseline at week 12 in the study eye mean diurnal IOP were −3.98 and −4.22 mm Hg in the mITT and PP populations, respectively (p<0.001).

The changes from baseline in the study eye mean diurnal IOP at weeks 4 and 8 were also clinically meaningful and statistically significant, ranging from −4.49 to −4.22 mm Hg for the mITT and from −4.64 to −4.14 mm Hg for the PP population, respectively.

Results similar to those seen in the overall mITT population were also observed for each age subgroup (≤65 years and >65 years) for the primary efficacy variable.

Sensitivity analyses demonstrated no meaningful differences in efficacy with or without patients from the excluded study site.

Brief Summary of Adverse Events:

A summary of patients with adverse events is provided in Table 14. A total of 54/121 (44.6%) patients experienced 1 or more adverse events. Of the 121 patients, 39 (32.2%) patients experienced treatment-related adverse events. The vast majority of patients who experienced adverse events had adverse events that were ocular in nature.

The maximum severity of adverse events was mild in 39/121 (32.2%) patients, moderate in 14/121 (11.6%) patients, and severe in 1/121 (0.8%) patient (adverse event of glaucoma, which was not considered treatment-related). A total of 7/121 (5.8%) patients were discontinued from the study due to adverse events (all of which were ocular in nature). The most commonly reported adverse events leading to discontinuation were conjunctival hyperaemia (3 patients), conjunctival disorder (2 patients), conjunctivitis allergic (2 patients), and eye pain (2 patients). No serious adverse events were reported.

TABLE 14

Summary of Patients with Adverse Events (Safety Population)

| | TRIPLE COMBINATION GROUP (N = 121) n (%) |
|---|---|
| All adverse events | 54 (44.6) |
| All ocular adverse events | 49 (40.5) |
| All serious adverse events | 0 |
| Treatment-related adverse events | 39 (32.2) |
| Treatment-related ocular adverse events | 38 (31.4) |
| Treatment-related serious adverse events | 0 |
| All adverse events by severity | |
| Missing | 0 |
| Mild | 39 (32.2) |
| Moderate | 14 (11.6) |
| Severe[a] | 1 (0.8) |
| N/A | 0 |
| Adverse events leading to death | 0 |
| Adverse events leading to discontinuation from study | 7 (5.8) |
| Ocular adverse events leading to discontinuation from study | 7 (5.8) |

Note:
For adverse event severity category, a patient is counted only once based on maximum severity of all adverse events.
[a] Severe adverse event was reported as 'glaucoma' (preferred term) and was described clinically as 'worsening of glaucoma'. This worsening of glaucoma was not considered treatment-related.

A total of 49/121 (40.5%) patients experienced ocular adverse events. Of the 121 patients, 38 (31.4%) patients experienced treatment-related ocular adverse events. The maximum severity of ocular adverse events was mild in 35/121 (28.9%) patients, moderate in 13/121 (10.7%) patients, and severe in 1/121 (0.8%) patient. A total of 7/121 (5.8%) patients were discontinued from the study due to ocular adverse events.

All Adverse Events:

Except for headache (4/121 [3.3%]), the most frequently reported adverse events (in 3 or more patients), were ocular in nature: conjunctival hyperaemia (20/121 [16.5%] patients), dry eye (6/121 [5.0%] patients), conjunctivitis (5/121 [4.1%] patients), conjunctival follicles (4/121 [3.3%] patients), eye pain (4/121 [3.3%] patients), lacrimation increased (4/121 [3.3%] patients), growth of eyelashes (3/121 [2.5%] patients), meibomian gland dysfunction (3/121 [2.5%] patients), and skin hyperpigmentation (3/121 [2.5%] patients).

Treatment-Related Adverse Events:

A summary of patients with treatment-related adverse events s by SOC and PT is provided in Table 15. A total of 39/121 (32.2%) patients experienced treatment-related adverse events and 38/121 (31.4%) patients experienced treatment-related ocular adverse events. Headache was the only non-ocular treatment-related adverse event.

TABLE 15

Summary of Patients with Treatment-related Adverse Events by System Organ Class and Preferred Term (Safety Population)

| System organ class<br>Preferred term | TRIPLE<br>COMBINATION<br>GROUP<br>(N = 121)<br>n (%) |
|---|---|
| Treatment-related adverse events | 39 (32.2) |
| Eye disorders | 36 (29.8) |
| Conjunctival hyperaemia | 17 (14.0) |
| Dry eye | 5 (4.1) |
| Conjunctival follicles | 4 (3.3) |
| Eye pain | 4 (3.3) |
| Lacrimation increased | 4 (3.3) |
| Growth of eyelashes | 3 (2.5) |
| Conjunctival disorder | 2 (1.7) |
| Conjunctivitis | 2 (1.7) |
| Conjunctivitis allergic | 2 (1.7) |
| Eye irritation | 2 (1.7) |
| Eye pruritus | 2 (1.7) |
| Meibomianitis | 2 (1.7) |
| Eyelid irritation | 1 (0.8) |
| Eyelids pruritus | 1 (0.8) |
| Keratitis | 1 (0.8) |
| Vision blurred | 1 (0.8) |
| Visual impairment | 1 (0.8) |
| Skin and subcutaneous tissue disorders | 2 (1.7) |
| Skin hyperpigmentation | 2 (1.7) |
| Nervous system disorders | 1 (0.8) |
| Headache | 1 (0.8) |

Note:
System organ class (SOC) and preferred terms (PT) are coded using the MedDRA version 15.0 dictionary. Preferred terms are sorted by descending frequencies. Within each combination of PT and SOC, a patient is counted at most once.

The most frequently reported treatment-related adverse events (in 3 or more patients) were conjunctival hyperaemia (17/121 [14.0%] patients), dry eye (5/121 [4.1%] patients), conjunctival follicles (4/121 [3.3%] patients), eye pain (4/121 [3.3%] patients), lacrimation increased (4/121 [3.3%] patients), and growth of eyelashes (3/121 [2.5%] patients).

Summary of Results:

Overall, 126 patients were enrolled in the study. A total of 121 patients were included in the mITT and safety populations; 5 patients (from study site 13001) were excluded from all analysis populations due to site termination for GCP violations. Of the 121 patients, 109 (90.1%) patients completed the study and 12 (9.9%) patients were discontinued from the study. In the mITT and safety populations, the mean (SD) age was 58.6 (11.44) years. The majority of patients (80/121 [66.1%]) were between ≥45 to ≤65 years of age. The majority of patients were male (76/121 [62.8%]). All patients had dark irides. All of the enrolled patients had a history of eye disorders. The most common eye disorder diagnosis was glaucoma. The specific glaucoma diagnoses were open angle glaucoma (62/121 [51.2%]) and angle closure glaucoma (44/121 [36.4%]). Sixteen (16/121 [13.2%]) patients had a diagnosis of ocular hypertension. Patient disposition and demographics of the PP population was similar to that of the mITT and safety populations.

Efficacy:

At week 12, TRIPLE COMBINATION provided a clinically meaningful and statistically significant additional IOP-lowering effect from the DUAL COMBINATION-treated baseline. The mean changes from baseline at week 12 in the study eye mean diurnal IOP were −3.98 and −4.22 mm Hg in the mITT and PP populations, respectively ($p<0.001$).

The changes from baseline in the study eye mean diurnal IOP at weeks 4 and 8 were also clinically meaningful and statistically significant, ranging from −4.49 to −4.22 mm Hg for the mITT and from −4.64 to −4.14 mm Hg for the PP population, respectively.

Results similar to those seen in the overall mITT population were also observed for each age subgroup (≤65 years and >65 years) for the primary efficacy variable.

Sensitivity analyses demonstrated no meaningful differences in efficacy with or without patients from the excluded study site.

Safety:

A total of 54/121(44.6%) patients experienced 1 or more adverse events. Of the 121 patients included in the safety population, 39 (32.2%) experienced treatment-related adverse events. A total of 38/121 (31.4%) patients experienced treatment-related ocular adverse events, the majority of which were mild or moderate in intensity.

The most frequently reported treatment-related adverse events (in 3 or more patients) were conjunctival hyperaemia (14.0%), dry eye (4.1%), conjunctival follicles (3.3%), eye pain (3.3%), lacrimation increased (3.3%), and growth of eyelashes (2.5%).

No deaths or other serious adverse events were reported during the study.

A total of 7/121 (5.8%) patients discontinued due to adverse events (all were ocular). The most common adverse events (reported in >1 patient) leading to discontinuation were conjunctival hyperaemia, conjunctival disorder, conjunctivitis allergic, and eye pain.

In general, no clinically significant change was observed in vital signs, cup/disc ratio, and visual acuity. Few patients were reported to have clinically significant findings (defined as ≥2 full severity grade increase from baseline in either eye during treatment) on slit-lamp biomicroscopy, with hyperaemia being the most frequently reported finding (7/121 [5.8%] patients).

The adverse events profile in each age subgroup (≤65 years and >65 years) was similar to that of the overall safety population.

Sensitivity analyses demonstrated no meaningful differences in safety with or without patients from the excluded study site.

CONCLUSION

Triple Combination provides a clinically meaningful and statistically significant additional IOP-lowering effect from a Dual Combination-treated baseline and has an acceptable safety and tolerability profile in Indian patients with glaucoma or ocular hypertension with elevated IOP.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. *"About" refers to variations in the concentrations of excipients and active agents which would be considered bioequivalent by a regulatory agency.

Recitation of ranges of values herein is merely intended to serve as a shorthand method of referring individually to each separate value falling within the range. Unless otherwise indicated herein, each individual value is incorporated into the specification as if it were individually recited herein. All methods disclosed herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are disclosed herein, including the best mode known to the inventors for carrying out the invention. Of course, variations on these described embodiments will become apparent to those of ordinary skill in the art upon reading the foregoing description. The inventor expects one of ordinary skill in the art to employ such variations as appropriate, and the inventors intend for the invention to be practiced otherwise than specifically disclosed herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for lowering intraocular pressure in patients suffering from elevated intraocular pressure who do not have adequate intraocular pressure control with mono or dual combination therapy, the method comprising administering to a patient a composition consisting essentially of about 0.01% w/v bimatoprost, about 0.15% w/v brimonidine tartrate, about 0.68% w/v timolol maleate, sodium phosphate dibasic heptahydrate, citric acid monohydrate, sodium chloride, and sodium hydroxide in an aqueous carrier.

2. The method of claim 1, wherein the composition consists of 0.01% w/v bimatoprost, 0.15% w/v brimonidine tartrate, 0.68% w/v timolol maleate, 1.5% w/v sodium phosphate dibasic heptahydrate, 0.025% w/v citric acid monohydrate, 0.35% w/v sodium chloride, and sodium hydroxide in an aqueous carrier.

3. The method of claim 2, wherein the composition further consists of 0.005% w/v benzalkonium chloride.

4. The method of claim 1 or 3, wherein the composition is administered twice daily.

5. The method of claim 1 or 3, wherein the composition is administered to a patient with a mean baseline IOP greater than 25 mmHg.

6. The method of claim 1 or 3, wherein the dual combination therapy is a fixed combination of 0.2% w/v brimonidine tartrate and 0.68% w/v timolol maleate.

* * * * *